US011079395B2

(12) United States Patent
Beshiri et al.

(10) Patent No.: US 11,079,395 B2
(45) Date of Patent: Aug. 3, 2021

(54) METHODS FOR PREDICTING MAJOR ADVERSE CARDIOVASCULAR EVENTS IN SUBJECTS WITH CORONARY ARTERY DISEASE

(71) Applicants: Abbott Laboratories, Abbott Park, IL (US); Emory University, Atlanta, GA (US)

(72) Inventors: Agim Beshiri, Abbott Park, IL (US); Arshed A. Quyyumi, Atlanta, GA (US)

(73) Assignees: Abbott Laboratories, Abbott Park, IL (US); Emory University, Atlanta, GA (US)

( * ) Notice: Subject to any disclaimer, the term of this patent is extended or adjusted under 35 U.S.C. 154(b) by 0 days.

(21) Appl. No.: 16/805,136

(22) Filed: Feb. 28, 2020

(65) Prior Publication Data
US 2020/0278357 A1 Sep. 3, 2020

Related U.S. Application Data

(60) Provisional application No. 62/812,560, filed on Mar. 1, 2019.

(51) Int. Cl.
*G01N 33/53* (2006.01)
*G01N 33/68* (2006.01)

(52) U.S. Cl.
CPC ..... *G01N 33/6893* (2013.01); *G01N 2800/32* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 5,006,309 A | 4/1991 | Khalil et al. | |
| 5,063,081 A | 11/1991 | Cozzette et al. | |
| 5,089,424 A | 2/1992 | Khalil et al. | |
| 5,292,636 A * | 3/1994 | Kung | C07K 16/2812 435/34 |
| 5,294,404 A | 3/1994 | Grandone et al. | |
| 6,438,498 B1 | 8/2002 | Opalsky et al. | |
| 7,838,250 B1 * | 11/2010 | Goix | G01N 21/6486 435/7.1 |
| 2003/0170881 A1 | 9/2003 | Davis et al. | |
| 2004/0018577 A1 | 1/2004 | Campbell et al. | |
| 2005/0054078 A1 | 10/2005 | Miller et al. | |
| 2006/0134713 A1 | 7/2006 | Rylatt et al. | |
| 2006/0160164 A1 | 7/2006 | Miller et al. | |
| 2011/0053179 A1 | 3/2011 | Datvvyler et al. | |

FOREIGN PATENT DOCUMENTS

| | | |
|---|---|---|
| EP | 2472258 | 7/2012 |
| WO | WO 2017075268 A1 | 5/2017 |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, pp. 1-7. (Year: 2014).*
Sabatine et al., Detection of acute changes in circulating troponin in the setting of transient stress test-induced myhocardial ischaemia using an ultrasensitive assay: results from TIMI 35, European Journal, 2009, 30, pp. 162-169. (Year: 2009).*
Choragudi et al., Does the Serum Cardiac Troponin I Level Increase With Stress Test-Induced Myocardial Ischemia? Heart Dis. Jul.-Aug. 2002, 4(4), pp. 216-219. (Year: 2002).*
Apple et al., "Cardiac Troponin Assays: Guide to Understanding Analytical Characteristics and Their Impact on Clinical Care." Clin Chem. Jan. 2017;63(1):73-81.
Apple et al., "Determination of 19 cardiac troponin I and T assay 99th percentile values from a common presumably healthy population." Clin Chem. Nov. 2012; 58(11):1574-81.
Apple et al., "Tissue specificity of cardiac troponin I, cardiac troponin T and creatine kinase-MB." Clin Chim Acta. Jun. 30, 1999; 284(2):151-9.
Aw et al., "Measurement of cardiac troponin I in serum with a new high-sensitivity assay in a large multi-ethnic Asian cohort and the impact of gender." Clin Chim Acta. Jun. 25, 2013; 422:26-8.
Defilippi et al., "Association of serial measures of cardiac troponin T using a sensitive assay with incident heart failure and cardiovascular mortality in older adults." JAMA. Dec. 8, 2010; 304(22):2494-502.
Delemos et al., "Association of troponin T detected with a highly sensitive assay and cardiac structure and mortality risk in the general population." JAMA. Dec. 8, 2010; 304(22):2503-12.
Everett et al., "High-sensitivity cardiac troponin I and B-type natriuretic Peptide as predictors of vascular events in primary prevention: impact of statin therapy." Circulation. May 26, 2015;131(21):1851-60.
Everett et al., "Troponin and Cardiac Events in Stable Ischemic Heart Disease and Diabetes." N Engl J Med. Aug. 13, 2015; 373(7):610-20.
Gray, "A Class of K-Sample Tests for Comparing the Cumulative Incidence of a Competing Risk." The Annals of Statistics Sep. 1988, 16(3):1141-1154.
Hammadah et al., "Use of High-Sensitivity Cardiac Troponin for the Exclusion of Inducible Myocardial Ischemia: A Cohort Study." Ann Intern Med. Dec. 4, 2018; 169(11):751-760.
Holly et al., "Single photon-emission computed tomography." J Nucl Cardiol. Oct. 2010; 17(5):941-73.

(Continued)

*Primary Examiner* — Gary Counts
(74) *Attorney, Agent, or Firm* — Casimir Jones, S.C.; Melissa E. Karabinis

(57) ABSTRACT

Provided herein are methods for predicting or determining whether a subject with coronary artery disease is likely to experience or develop a major adverse cardiovascular event (MACE) based on determining cardiac troponin (cTnI) levels in a human at rest and during or after exercise.

9 Claims, 3 Drawing Sheets

Specification includes a Sequence Listing.

(56) References Cited

OTHER PUBLICATIONS

Keller et al., "High-sensitivity cardiac troponin assays: finally ready for prime time?" Nat Rev Cardiol. Mar. 2019;16(3):135-136.

Keller et al., "Sensitive troponin I assay in early diagnosis of acute myocardial infarction." N Engl J Med. Aug. 27, 2009;361(9):868-77.

Keller et al., "Serial changes in highly sensitive troponin I assay and early diagnosis of myocardial infarction." JAMA. Dec. 28, 2011; 306(24):2684-93.

Mills et al., "Implementation of a sensitive troponin I assay and risk of recurrent myocardial infarction and death in patients with suspected acute coronary syndrome." JAMA. Mar. 23, 2011;305(12):1210-6.

NACB Writing Group et al., "National Academy of Clinical Biochemistry laboratory medicine practice guidelines: use of cardiac troponin and B-type natriuretic peptide or N-terminal proB-type natriuretic peptide for etiologies other than acute coronary syndromes and heart failure." Clin Chem. Dec. 2007;53(12):2086-96.

Omland et al., "A sensitive cardiac troponin T assay in stable coronary artery disease." N Engl J Med. Dec. 24, 2009;361(26): 2538-47.

Pencina et al., "Evaluating the added predictive ability of a new marker: from area under the ROC curve to reclassification and beyond." Stat Med. Jan. 30, 2008; 27(2):157-72.

Pencina et al., "Extensions of net reclassification improvement calculations to measure usefulness of new biomarkers." Statistics in Med. Jan. 15, 2011; 30(1):11-21.

Ramadan et al., "Myocardial ischemia during mental stress: role of coronary artery disease burden and vasomotion." J Am Heart Assoc. Oct. 21, 2013; 2(5):e000321.

Sandesara et al., "Comparison of the Association Between High-Sensitivity Troponin I and Adverse Cardiovascular Outcomes in Patients With Versus Without Chronic Kidney Disease." Am J Cardiol. Jun. 15, 2018; 121(12):1461-1466.

Saunders et al., "Cardiac troponin T measured by a highly sensitive assay predicts coronary heart disease, heart failure, and mortality in the Atherosclerosis Risk in Communities Study." Circulation. Apr. 5, 2011; 123(13):1367-76.

Sherwood & Newby "High-sensitivity troponin assays: evidence, indications, and reasonable use." J Am Heart Assoc. Jan. 27, 2014; 3(1):e000403.

Tahhan et al., "High-Sensitivity Troponin I Levels and Coronary Artery Disease Severity, Progression, and Long-Term Outcomes." J Am Heart Assoc. Feb. 21, 2018;7(5):e007914.

Thygesen et al., "Fourth Universal Definition of Myocardial Infarction (2018)." Circulation. Nov. 13, 2018; 138(20):e618-e651.

Uno et al., "A unified inference procedure for a class of measures to assess improvement in risk prediction systems with survival data." Stat Med. Jun. 30, 2013; 32(14):2430-42.

Uno et al., "On the C-statistics for evaluating overall adequacy of risk prediction procedures with censored survival data." Stat Med. May 10, 2011; 30(10):1105-17.

Vaccarino et al., "Sex Differences in Mental Stress-Induced Myocardial Ischemia in Patients With Coronary Heart Disease." *J Am Heart Assoc.* 2016, 5(9).

Yeboah et al., "Predictive value of brachial flow-mediated dilation for incident cardiovascular events in a population-based study: the multi-ethnic study of atherosclerosis." Circulation. Aug. 11, 2009;120(6):502-9.

Zeller et al., "High population prevalence of cardiac troponin I measured by a high-sensitivity assay and cardiovascular risk estimation: the MORGAM Biomarker Project Scottish Cohort." Eur Heart J. Feb. 2014;35(5):271-81.

\* cited by examiner

METHODS FOR PREDICTING MAJOR ADVERSE CARDIOVASCULAR EVENTS IN SUBJECTS WITH CORONARY ARTERY DISEASE

CROSS-REFERENCE TO RELATED APPLICATIONS

This application claims the benefit of U.S. Provisional Patent Application No. 62/812,560, filed Mar. 1, 2019, the disclosure of which is incorporated by reference herein.

GOVERNMENT FUNDING

This invention was made with Government support under Grant Nos. P01 HL101398, R01 HL109413, R01HL109413-02S1, R01HL125246, K24HL077506, K24 MH076955, UL1TR000454, KL2TR000455, K23HL127251, and T32HL130025A awarded by the National Institutes of Health. The Federal Government has certain rights to the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 824 Byte ASCII (Text) file named "2020-02-28_37611-202_SQL_ST25," created on Feb. 28, 2020.

FIELD

The present disclosure relates to methods for predicting or determining whether a subject with coronary artery disease is likely to experience or develop a major adverse cardiovascular event (MACE) based on comparing the concentration or levels of cardiac troponin I (cTnI) determined in one or more assays before a stress test and then during or after a stress test.

BACKGROUND

Cardiac troponin (cTn) I and T are regulatory proteins that constitute the contractile apparatus of cardiomyocytes (Apple, F S., Synthe Clin. Chin. Acta, 284(2): 151-9 (1999); Apple, et al., Clin. Chem., 73-81 (2017)). High circulating levels of these proteins, measured using conventional assays, signify myocardial necrosis and form the cornerstone for the diagnosis of myocardial infarction (MI) and for guiding treatment strategies (Thygesen K., et al., Circulation, 138(20):e618-e51 (2018)). Recent technical advances have resulted in development of high-sensitivity (hs) assays that permit measurements of troponins at levels below the detection limits of conventional assays (Keller et al., Nat. Rev. Cardiol., 2018).

Measurement of hs-cTn in patients with chest pain can provide an earlier diagnosis of MI and these measurements are beginning to be widely implemented in the emergency setting (Mills, et al., JAMA, 305(12):1210-6 (2011); Keller et al., N. Engl. J. Med., 361(9):868-77 (2009)). Several studies have investigated the prognostic value of hs-cTn levels in otherwise healthy subjects and in those with stable coronary artery disease (CAD) (Sherwood et al., J. Am. Heart Assoc., 3(1):e000403 (2014); deFilippi et al., JAMA, 304(22):3494-502 (2010); deLemos et al., JAMA, 304(22): 2503-12 (2010); Saunders et al., Circulation, 123(13):1367-76 (2011)). These studies demonstrate that elevated hs-cTn levels are associated with the underlying burden of coronary atherosclerosis, more rapid progression of CAD and with incident adverse cardiovascular events (Omland et al., N. Engl. J. Med., 361(26):2538-47 (2009); Samman Tahhan, et al., J. Am. Heart Assoc., 7(5):2018; Everett, et al., N. Engl. J. Med., 373(7):610-20 (2015); Everett, et al., Circulation, 131(21):1851-60 (2015); Sandesara et al., Am. J. Cardiol., 121(12): 1461-6 (2018)). Furthermore, very low levels of high-sensitivity cardiac troponin (hs-cTnI) are useful in excluding inducible myocardial ischemia in patients with stable CAD and are associated with excellent prognosis, free of incident adverse cardiovascular events (Hammadah et al., Ann. Intern Med., 169(11):751-60 (2018)).

While it is known that hs-cTn levels increase with exercise, with mental stress and with rapid atrial pacing in patients and that these changes correlate with the magnitude of myocardial ischemia, it is unknown in the art whether the magnitude of change in hs-cTn levels in subjects with CAD serves any useful prognostic purpose.

SUMMARY

The present disclosure relates to a determining whether a subject with coronary artery disease is likely to experience a MACE. The method comprises the steps of: (a) performing at least one assay to determine a level of cTnI in a sample obtained from a subject prior to performing a stress test; (b) conducting a stress test on the subject; (c) performing at least one assay to determine the level of cTnI in a sample obtained from the subject during or after the stress test: (d) comparing the levels of cTnI before and during after the stress test; and E determining that the subject is (i) likely to experience a MACE if the level of cTnI measured during or after the stress test has increased at least about 10% when compared with the level of cTnI measured before the stress test; or (ii) not likely to experience a MACE if the level of cTnI measure during or after the stress test has not increased by at least about 10% when compared with the level of cTnI measured before the stress test.

In the above method, in one aspect, the subject has stable coronary artery disease. In another aspect, the subject has unstable coronary artery disease.

In another aspect of the above method, the assay is performed during the stress test. In another aspect, the assay is performed after the stress test. In yet another aspect, an assay is performed during the stress test and one or more assays are performed after the stress test.

In yet another aspect of the above method, the sample is a biological sample. In yet a further aspect, the sample is a whole blood sample. In still yet another aspect, the sample is a serum sample. In still yet a further aspect, the sample is a plasma sample.

In yet another aspect of the above method, the method involves determining whether the subject is:

a. likely to experience a MACE if the level of cTnI measured during or after the stress test has increased at least about 11%, or (ii) not likely to experience a MACE if the level of cTnI measure during or after the stress test has not increased by at least about 11% when compared with the level of cTnI measured before the stress test;

b. likely to experience a MACE if the level of cTnI measured during or after the stress test has increased at least about 12%, or (ii) not likely to experience a MACE if the level of cTnI measure during or after the stress test has not increased by at least about 12% when compared with the level of cTnI measured before the stress test;
c. likely to experience a MACE if the level of cTnI measured during or after the stress test has increased at least about 13%, or (ii) not likely to experience a MACE if the level of cTnI measure during or after the stress test has not increased by at least about 13% when compared with the level of cTnI measured before the stress test;
d. likely to experience a MACE if the level of cTnI measured during or after the stress test has increased at least about 14%, or (ii) not likely to experience a MACE if the level of cTnI measure during or after the stress test has not increased by at least about 14% when compared with the level of cTnI measured before the stress test;
e. likely to experience a MACE if the level of cTnI measured during or after the stress test has increased at least about 15%, or (ii) not likely to experience a MACE if the level of cTnI measure during or after the stress test has not increased by at least about 15% when compared with the level of cTnI measured before the stress test;
f. likely to experience a MACE if the level of cTnI measured during or after the stress test has increased at least about 16%, or (ii) not likely to experience a MACE if the level of cTnI measure during or after the stress test has not increased by at least about 16% when compared with the level of cTnI measured before the stress test;
g. likely to experience a MACE if the level of cTnI measured during or after the stress test has increased at least about 17%, or (ii) not likely to experience a MACE if the level of cTnI measure during or after the stress test has not increased by at least about 17% when compared with the level of cTnI measured before the stress test;
h. likely to experience a MACE if the level of cTnI measured during or after the stress test has increased at least about 18%, or (ii) not likely to experience a MACE if the level of cTnI measure during or after the stress test has not increased by at least about 18% when compared with the level of cTnI measured before the stress test;
i. likely to experience a MACE if the level of cTnI measured during or after the stress test has increased at least about 19%, or (ii) not likely to experience a MACE if the level of cTnI measure during or after the stress test has not increased by at least about 19% when compared with the level of cTnI measured before the stress test;
j. likely to experience a MACE if the level of cTnI measured during or after the stress test has increased at least about 20%, or (ii) not likely to experience a MACE if the level of cTnI measure during or after the stress test has not increased by at least about 20% when compared with the level of cTnI measured before the stress test;
k. likely to experience a MACE if the level of cTnI measured during or after the stress test has increased at least about 21%, or (ii) not likely to experience a MACE if the level of cTnI measure during or after the stress test has not increased by at least about 21% when compared with the level of cTnI measured before the stress test;
l. likely to experience a MACE if the level of cTnI measured during or after the stress test has increased at least about 22%, or (ii) not likely to experience a MACE if the level of cTnI measure during or after the stress test has not increased by at least about 22% when compared with the level of cTnI measured before the stress test;
m. likely to experience a MACE if the level of cTnI measured during or after the stress test has increased at least about 23%, or (ii) not likely to experience a MACE if the level of cTnI measure during or after the stress test has not increased by at least about 23% when compared with the level of cTnI measured before the stress test;
n. likely to experience a MACE if the level of cTnI measured during or after the stress test has increased at least about 24%, or (ii) not likely to experience a MACE if the level of cTnI measure during or after the stress test has not increased by at least about 24% when compared with the level of cTnI measured before the stress test;
o. likely to experience a MACE if the level of cTnI measured during or after the stress test has increased at least about 25%, or (ii) not likely to experience a MACE if the level of cTnI measure during or after the stress test has not increased by at least about 25% when compared with the level of cTnI measured before the stress test;
p. likely to experience a MACE if the level of cTnI measured during or after the stress test has increased at least about 26%, or (ii) not likely to experience a MACE if the level of cTnI measure during or after the stress test has not increased by at least about 26% when compared with the level of cTnI measured before the stress test;
q. likely to experience a MACE if the level of cTnI measured during or after the stress test has increased at least about 27%, or (ii) not likely to experience a MACE if the level of cTnI measure during or after the stress test has not increased by at least about 27% when compared with the level of cTnI measured before the stress test;
r. likely to experience a MACE if the level of cTnI measured during or after the stress test has increased at least about 28%, or (ii) not likely to experience a MACE if the level of cTnI measure during or after the stress test has not increased by at least about 28% when compared with the level of cTnI measured before the stress test;
s. likely to experience a MACE if the level of cTnI measured during or after the stress test has increased at least about 29%, or (ii) not likely to experience a MACE if the level of cTnI measure during or after the stress test has not increased by at least about 29% when compared with the level of cTnI measured before the stress test;
t. likely to experience a MACE if the level of cTnI measured during or after the stress test has increased at least about 30%, or (ii) not likely to experience a MACE if the level of cTnI measure during or after the stress test has not increased by at least about 30% when compared with the level of cTnI measured before the stress test;
u. likely to experience a MACE if the level of cTnI measured during or after the stress test has increased at least about 31%, or (ii) not likely to experience a MACE if the level of cTnI measure during or after the stress test has not increased by at least about 31% when compared with the level of cTnI measured before the stress test;
v. likely to experience a MACE if the level of cTnI measured during or after the stress test has increased at least about 32%, or (ii) not likely to experience a MACE if the level of cTnI measure during or after the stress test has not increased by at least about 32% when compared with the level of cTnI measured before the stress test;
w. likely to experience a MACE if the level of cTnI measured during or after the stress test has increased at least about 33%, or (ii) not likely to experience a MACE if the level of cTnI measure during or after the stress test has not increased by at least about 33% when compared with the level of cTnI measured before the stress test;
x. likely to experience a MACE if the level of cTnI measured during or after the stress test has increased at least about 34%, or (ii) not likely to experience a MACE if the level of cTnI measure during or after the stress test has not increased by at least about 34% when compared with the level of cTnI measured before the stress test;
y. likely to experience a MACE if the level of cTnI measured during or after the stress test has increased at least about 35%, or (ii) not likely to experience a MACE if the level of cTnI measure during or after the stress test has not increased by at least about 35% when compared with the level of cTnI measured before the stress test;
z. likely to experience a MACE if the level of cTnI measured during or after the stress test has increased at least about 36%, or (ii) not likely to experience a MACE if the level of cTnI measure during or after the stress test has not increased by at least about 36% when compared with the level of cTnI measured before the stress test;
aa. likely to experience a MACE if the level of cTnI measured during or after the stress test has increased at least about 37%, or (ii) not likely to experience a MACE if the level of cTnI measure during or after the stress test has not increased by at least about 37% when compared with the level of cTnI measured before the stress test;
bb. likely to experience a MACE if the level of cTnI measured during or after the stress test has increased at least about 38%, or (ii) not likely to experience a MACE if the level of cTnI measure during or after the stress test has not increased by at least about 38% when compared with the level of cTnI measured before the stress test;
cc. likely to experience a MACE if the level of cTnI measured during or after the stress test has increased at least about 39%, or (ii) not likely to experience a MACE if the level of cTnI measure during or after the stress test has not increased by at least about 39% when compared with the level of cTnI measured before the stress test;
dd. likely to experience a MACE if the level of cTnI measured during or after the stress test has increased at least about 40%, or (ii) not likely to experience a MACE if the level of cTnI measure during or after the stress test has not increased by at least about 40% when compared with the level of cTnI measured before the stress test;
ee. likely to experience a MACE if the level of cTnI measured during or after the stress test has increased at least about 41%, or (ii) not likely to experience a MACE if the level of cTnI measure during or after the stress test has not increased by at least about 41% when compared with the level of cTnI measured before the stress test;
ff. likely to experience a MACE if the level of cTnI measured during or after the stress test has increased at least about 42%, or (ii) not likely to experience a MACE if the level of cTnI measure during or after the stress test has not increased by at least about 42% when compared with the level of cTnI measured before the stress test;
gg. likely to experience a MACE if the level of cTnI measured during or after the stress test has increased at least about 43%, or (ii) not likely to experience a MACE if the level of cTnI measure during or after the stress test has not increased by at least about 43% when compared with the level of cTnI measured before the stress test;
hh. likely to experience a MACE if the level of cTnI measured during or after the stress test has increased at least about 44%, or (ii) not likely to experience a MACE if the level of cTnI measure during or after the stress test has not increased by at least about 44% when compared with the level of cTnI measured before the stress test;
ii. likely to experience a MACE if the level of cTnI measured during or after the stress test has increased at least about 45%, or (ii) not likely to experience a MACE if the level of cTnI measure during or after the stress test has not increased by at least about 45% when compared with the level of cTnI measured before the stress test;
jj. likely to experience a MACE if the level of cTnI measured during or after the stress test has increased at least about 46%, or (ii) not likely to experience a MACE if the level of cTnI measure during or after the stress test has not increased by at least about 46% when compared with the level of cTnI measured before the stress test;
kk. likely to experience a MACE if the level of cTnI measured during or after the stress test has increased at least about 47%, or (ii) not likely to experience a MACE if the level of cTnI measure during or after the stress test has not increased by at least about 47% when compared with the level of cTnI measured before the stress test;
ll. likely to experience a MACE if the level of cTnI measured during or after the stress test has increased at least about 48%, or (ii) not likely to experience a MACE if the level of cTnI measure during or after the stress test has not increased by at least about 48% when compared with the level of cTnI measured before the stress test;
mm. likely to experience a MACE if the level of cTnI measured during or after the stress test has increased at least about 49%, or (ii) not likely to experience a MACE if the level of cTnI measure during or after the stress test has not increased by at least about 49% when compared with the level of cTnI measured before the stress test; or
nn. likely to experience a MACE if the level of cTnI measured during or after the stress test has increased at least about 50%, or (ii) not likely to experience a MACE if the level of cTnI measure during or after the stress test has not increased by at least about 50% when compared with the level of cTnI measured before the stress test.

In yet another aspect, in the above method, the at least one assay performed before the stress test and the at least one assay performed after the stress test are the same. Alternatively, in still a further aspect, the at least one assay performed before the stress test and the at least one assay performed after the stress test are different assays.

In still a further aspect, in the above method, the at least one assay performed before the stress test is an immunoassay, a clinical chemistry assay, a point-of-care assay or a single molecule detection assay. In still yet a further aspect, at least one assay performed during or after the stress test is an immunoassay, a clinical chemistry assay, a point-of-care assay or a single molecule detection assay. In still yet a further aspect, the concentration or level of cTnI is determined using a high sensitivity cardiac troponin I assay.

DETAILED DESCRIPTION

Figure 1A:
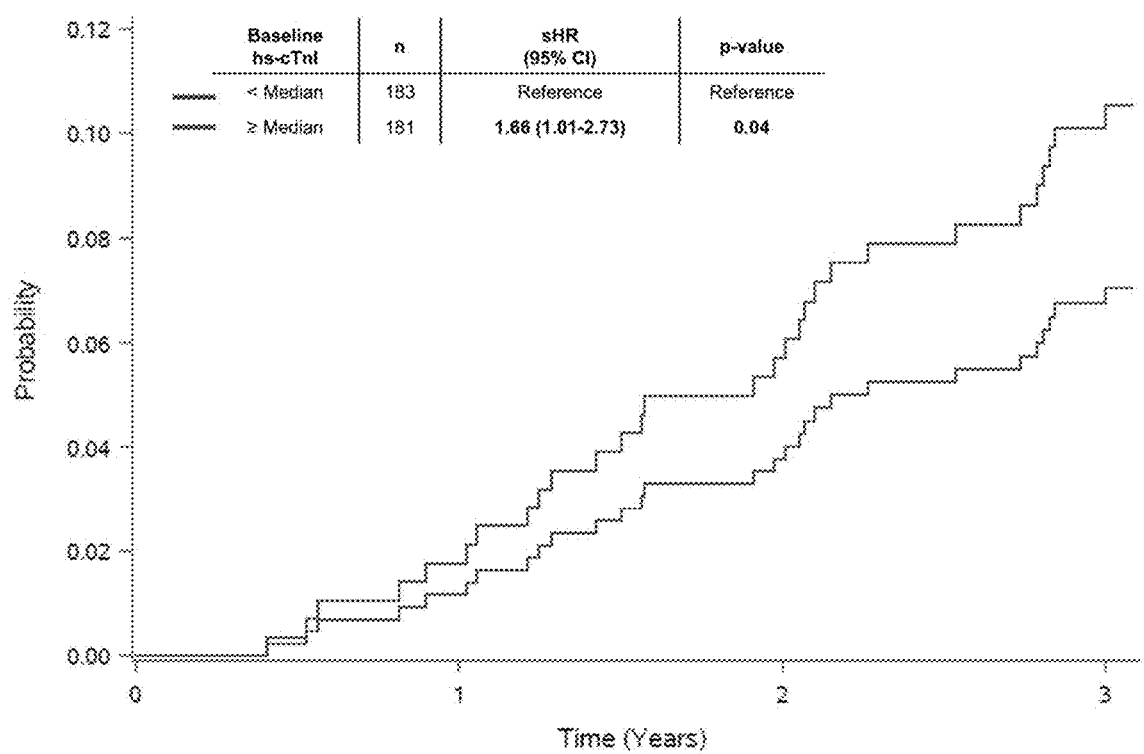
FIGS. 1A-IC are graphs showing the adjusted cumulative incidence of major adverse cardiovascular events (MACE) by baseline (below or above median) high-sensitivity cardiac troponin I (hs-cTnI) (FIG. 1A); hs-cTnI response to exercise stress testing (below or above 20% increase) (FIG. 1B); and four categories combining baseline and hs-cTnI response to stress (FIG. 1C). MACE is defined as a combination of cardiovascular (CV) death, MI and unstable angina with revascularization. The median baseline hs-cTnI was 4 ng/mL. sHR represents the risk of endpoints for the comparison versus the reference groups while treating non-cardiovascular death as competing risk. P-values were generated from cumulative incidence function homogeneity test of Gray. Abbreviations: sHR (Sub-distribution Hazard Ration); CI (Confidence Interval).

The present disclosure relates to methods of using elevated levels of cTnI in subjects with CAD (such as stable CAD) with or after exercise to predict or determine whether such subjects are likely to experience or suffer one or more MACEs.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Affinity matured antibody" is used herein to refer to an antibody with one or more alterations in one or more CDRs, which result in an improvement in the affinity (i.e., $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., *BioTechnology*, 10: 779-783 (1992) describes affinity maturation by VH and VL domain shuffling. Random mutagenesis of CDR and/or framework residues is described by Barbas et al., *Proc. Nat. Acad. Sci. USA*, 91: 3809-3813 (1994): Schier et al., *Gene*, 169: 147-155 (1995); Yelton et al., *J. Inmmunol.*, 155: 1994-2004 (1995); Jackson et al., *J. Immunol.*, 154(7): 3310-3319 (1995); and Hawkins et al, J. Mol. Biol., 226; 889-896 (1992). Selective mutation at selective mutagenesis positions and at contact or hypermutation positions with an activity-enhancing amino acid residue is described in U.S. Pat. No. 6,914,128 B1.

"Antibody" and "antibodies" as used herein refers to monoclonal antibodies, monospecific antibodies (e.g., which can either be monoclonal, or may also be produced by other means than producing them from a common germ cell), multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')$_2$ fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., *Nature Biotechnology*, 25(11): 1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-TnI antibody).

"Antibody fragment" as used herein refers to a portion of an intact antibody comprising the antigen-binding site or variable region. The portion does not include the constant heavy chain domains (i.e., CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An AUC of 1 represents a perfect test, whereas an AUC of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Bead" and "particle" are used herein interchangeably and refer to a substantially spherical solid support. One example of a bead or particle is a microparticle. Microparticles that can be used herein can be any type known in the art. For example, the bead or particle can be a magnetic bead or magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO-Fe_2O_3$). Beads can have a solid core portion that is magnetic and is surrounded by one or more non-magnetic layers. Alternately, the magnetic portion can be a layer around a non-magnetic core. The microparticles can be of any size that would work in the methods described herein, e.g., from about 0.75 to about 5 nm, or from about 1 to about 5 nm, or from about 1 to about 3 nm.

"Binding protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature. 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

"CDR" is used herein to refer to the "complementarity determining region" within an antibody variable sequence. There are three CDRs in each of the variable regions of the heavy chain and the light chain. Proceeding from the N-terminus of a heavy or light chain, these regions are denoted "CDR1", "CDR2", and "CDR3", for each of the variable regions. The term "CDR set" as used herein refers to a group of three CDRs that occur in a single variable region that binds the antigen. An antigen-binding site, therefore, may include six CDRs, comprising the CDR set from each of a heavy and a light chain variable region. A polypeptide comprising a single CDR. (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/ solution, a substrate (e.g., as a solution), a stop solution, and the like that can be included in a kit for assay of a test sample, such as a patient urine, whole blood, serum or plasma sample, in accordance with the methods described herein and other methods known in the art. Some components can be in solution or lyophilized for reconstitution for use in an assay.

"Controls" as used herein generally refers to a reagent whose purpose is to evaluate the performance of a measurement system in order to assure that it continues to produce results within permissible boundaries (e.g., boundaries ranging from measures appropriate for a research use assay on one end to analytic boundaries established by quality specifications for a commercial assay on the other end). To accomplish this, a control should be indicative of patient results and optionally should somehow assess the impact of error on the measurement (e.g., error due to reagent stability, calibrator variability, instrument variability, and the like). An example of a "control subject" is a subject that has coronary artery disease but has not experienced a MACE. In another example, a "control subject" is a subject that has stable coronary artery disease and has not experienced a MACE.

"Coronary artery disease" as used herein encompasses all forms of atherosclerotic disease affecting the coronary arteries. The phrase "stable coronary artery disease" refers to coronary artery disease in which the subject exhibits one or more of an established pattern of angina pectoris, a history of myocardial infarction (MI), and/or the presence of plaque documented by catheterization. For example, with stable coronary artery disease, chest pain may occur during or as a result of certain activities and then disappear after a period of rest. In contrast, subjects suffering from "unstable coronary artery disease" may experience chest pain at unpredictable intervals, which may or may not become more severe or frequent, last longer, or occur or continue to occur while resting.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g., a protein domain, said protein domain being linked by covalent or noncovalent bonds. The linkage can be based on genetic fusion according to the methods known in the art. The additional domain present in the fusion protein comprising the antibody may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g., a cytokine or growth hormone), a chemical agent, a peptide, a protein, or a drug, for example.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig." Such a DVD-Ig binding protein is thus tetrameric and reminiscent of an IgG molecule, but provides more antigen binding sites than an IgG molecule.

Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., *Nature Biotech.*, 25: 1290-1297 (2007). A preferred example of such DVD-Ig molecules comprises a heavy chain that comprises the structural formula VD1-(X1)n-VD2-C—(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C—(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of cTnI. Non-limiting examples of a DVD-Ig binding protein include a DVD-Ig binding protein that binds one or more epitopes of cTnI, a DVD-Ig binding protein that binds an epitope of a human cTnI and an epitope of cTnI of another species (for example, mouse), and a DVD-Ig binding protein that binds an epitope of a human cTnI and an epitope of another target molecule.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"Fragment antigen-binding fragment" or "Fab fragment" as used herein refers to a fragment of an antibody that binds to antigens and that contains one antigen-binding site, one complete light chain, and part of one heavy chain. Fab is a monovalent fragment consisting of the VL, VH, CL and CH1 domains. Fab is composed of one constant and one variable domain of each of the heavy and the light chain. The variable domain contains the paratope (the antigen-binding site), comprising a set of complementarity determining regions, at the amino terminal end of the monomer. Each arm of the Y thus binds an epitope on the antigen. Fab fragments can be generated such as has been described in the art, e.g., using the enzyme papain, which can be used to cleave an immunoglobulin monomer into two Fab fragments and an Fc fragment, or can be produced by recombinant means.

"F(ab')$_2$ fragment" as used herein refers to antibodies generated by pepsin digestion of whole IgG antibodies to remove most of the Fc region while leaving intact some of the hinge region. F(ab')$_2$ fragments have two antigen-binding F(ab) portions linked together by disulfide bonds, and therefore are divalent with a molecular weight of about 110 kDa. Divalent antibody fragments (F(ab')$_2$ fragments) are smaller than whole IgG molecules and enable a better penetration into tissue thus facilitating better antigen recognition in immunohistochemistry. The use of F(ab')$_2$ fragments also avoids unspecific binding to Fc receptor on live cells or to Protein A/G. F(ab')$_2$ fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol:// vbase.mrc-cpe.cam.ac.uk/) or in the international ImMunoGeneTics® (IMGT®) information system (hypertext transfer protocol://imgt.cines.fr/texts/IMGTrepertoire/ LocusGenes/).

"Functional antigen binding site" as used herein may mean a site on a binding protein (e.g., an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"Humanized antibody" is used herein to describe an antibody that comprises heavy and light chain variable region sequences from a non-human species (e.g., a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, *From Genes to Clones* (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Isolated polynucleotide" as used herein may mean a polynucleotide (e.g., of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as $^3H$, $^{14}C$, $^{32}P$, $^{33}P$, $^{35}S$, $^{90}Y$, $^{99}Tc$, $^{111}In$, $^{125}I$, $^{131}I$, $^{177}Lu$, $^{166}Ho$, and $^{153}Sm$), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2nd ed., Springer Verlag, N.Y. (1997), and in Haugland, *Handbook of Fluorescent Probes and Research Chemicals* (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., *Bioorg. Med. Chem. Lett.* 4: 2313-2317 (2004); Adamczyk et al., *Biorg. Med. Chem. Lett.* 14: 3917-3921 (2004); and Adamczyk et al., *Org. Lett.* 5: 3779-3782 (2003)).

In one aspect, the acridinium compound is an acridinium-9-carboxamide. Methods for preparing acridinium 9-carboxamides are described in Mattingly, *J. Biolumin. Chemilumin.* 6: 107-114 (1991); Adamczyk et al., *J. Org. Chem.* 63: 5636-5639 (1998); Adamczyk et al., *Tetrahedron* 55: 10899-10914 (1999); Adamczyk et al., *Org. Lett.* 1: 779-781 (1999); Adamczyk et al., *Bioconjugate Chem.* 11: 714-724 (2000); Mattingly et al., *In Luminescence Biotechnology: Instruments and Applications*; Dyke, K. V. Ed.; CRC Press: Boca Raton, pp. 77-105 (2002); Adamczyk et al., *Org. Lett.* 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., *Photochem. Photobiol.*, 4: 1111-21 (1965); Razavi et al., *Luminescence* 15: 245-249 (2000); Razavi et al., *Luminescence* 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, *High Throughput Bioanalytical Sample Preparation. Methods and Automation Strategies*, Elsevier (2003)). The amount of protein removed or separated from the test sample can be about 40%, about 45%, about 50%, about 55%, about 60%, about 65%, about 70%, about 75%, about 80%, about 85%, about 900, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Linking sequences can be used for many purposes, including in recombinant Fabs. Exemplary linking sequences include, but are not limited to: (i) Histidine (His) tags, such as a 6×=His tag, which has an amino acid sequence of HHHHHH (SEQ ID NO: 1), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO: 2) and derivatives thereof (e.g., ADDDDK (SEQ ID NO: 3), etc.); (iii) Miscellaneous sequences can be used to link or connect the light and/or heavy chain variable regions of single chain variable region fragments. Examples of other linking sequences can be found in Bird et al., *Science* 242: 423-426 (1988); Huston et al., *PNAS USA* 85: 5879-5883 (1988); and McCafferty et al., *Nature* 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Major adverse cardiac event" or "MACE" as used herein refers to at least one of cardiovascular death, myocardial infarction (MI), unstable angina with revascularization or any combinations thereof.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Point-of-care device" refers to a device used to provide medical diagnostic testing at or near the point-of-care (namely, outside of a laboratory), at the time and place of patient care (such as in a hospital, physician's office, urgent or other medical care facility, a patient's home, a nursing home and/or a long-term care and/or hospice facility). Examples of point-of-care devices include those produced by Abbott Laboratories (Abbott Park, Ill.) (e.g., i-STAT and i-STAT Alinity, Universal Biosensors (Rowville, Australia) (see US 2006/0134713), Axis-Shield PoC AS (Oslo, Norway) and Clinical Lab Products (Los Angeles, USA).

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a reference level or control level (e.g., "low," "medium," or "high" levels), can be used. Multiple calibrators (i.e., more than one calibrator or a varying amount of calibrator(s)) can be used in conjunction to comprise a "sensitivity panel."

A "receiver operating characteristic" curve or "ROC" curve refers to a graphical plot that illustrates the performance of a binary classifier system as its discrimination threshold is varied. For example, a ROC curve can be a plot of the true positive rate against the false positive rate for the different possible cutoff points of a diagnostic test. It is created by plotting the fraction of true positives out of the positives (TPR=true positive rate) vs. The fraction of false positives out of the negatives (FPR=false positive rate), at various threshold settings. TPR is also known as sensitivity, and FPR is one minus the specificity or true negative rate. The ROC curve demonstrates the tradeoff between sensitivity and specificity (any increase in sensitivity will be accompanied by a decrease in specificity); the closer the curve follows the left-hand border and then the top border of the ROC space, the more accurate the test; the closer the curve comes to the 45-degree diagonal of the ROC space, the less accurate the test; the slope of the tangent line at a cutoff point gives the likelihood ratio (LR) for that value of the test; and the area under the curve is a measure of test accuracy.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., *Nature Biotechnology*, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Reference level" as used herein refers to an assay cutoff value that is used to assess diagnostic, prognostic, or therapeutic efficacy and that has been linked or is associated herein with various clinical parameters (e.g., presence of disease, stage of disease, severity of disease, progression, non-progression, or improvement of disease, etc.). It is well-known that reference levels may vary depending on the nature of the immunoassay (e.g., antibodies employed, reaction conditions, sample purity, etc.) and that assays can be compared and standardized. It further is well within the ordinary skill of one in the art to adapt the disclosure herein for other immunoassays to obtain immunoassay-specific reference levels for those other immunoassays based on the description provided by this disclosure. Whereas the precise value of the reference level may vary between assays, the findings as described herein should be generally applicable and capable of being extrapolated to other assays.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "test sample," "biological sample", "specimen," "sample from a subject," and "patient sample" as used herein may be used interchangeable and may be a sample of blood such as whole blood, tissue, urine, serum, plasma, amniotic fluid, cerebrospinal fluid, placental cells or tissue, endothelial cells, leukocytes, or monocytes. In some embodiments the sample is whole blood. In some embodiments the sample is plasma. In other embodiments, the sample is serum. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

A variety of cell types, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, red blood cells, platelets, interstitial fluid, cerebral spinal fluid, etc. Cell types and tissues may also include lymph fluid, cerebrospinal fluid, a fluid collected by A tissue or cell type may be provided by removing a sample of cells from a human and a non-human animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

As used herein the term "single molecule detection" refers to the detection and/or measurement of a single molecule of an analyte in a test sample at very low levels of concentration (such as pg/mL or femtogram/mL levels). A number of different single molecule analyzers or devices are known in the art and include nanopore and nanowell devices. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety.

"Solid phase" or "solid support" as used interchangeably herein, refers to any material that can be used to attach and/or attract and immobilize (1) one or more capture agents or capture specific binding partners, or (2) one or more detection agents or detection specific binding partners. The solid phase can be chosen for its intrinsic ability to attract and immobilize a capture agent. Alternatively, the solid phase can have affixed thereto a linking agent that has the ability to attract and immobilize the (1) capture agent or capture specific binding partner, or (2) detection agent or detection specific binding partner. For example, the linking agent can include a charged substance that is oppositely charged with respect to the capture agent (e.g., capture specific binding partner) or detection agent (e.g., detection specific binding partner) itself or to a charged substance conjugated to the (1) capture agent or capture specific binding partner or (2) detection agent or detection specific binding partner. In general, the linking agent can be any binding partner (preferably specific) that is immobilized on (attached to) the solid phase and that has the ability to immobilize the (1) capture agent or capture specific binding partner, or (2) detection agent or detection specific binding partner through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes and fragments thereof, whether isolated or recombinantly produced.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus or rhesus monkey, chimpanzee, etc.) and a human). In some embodiments, the subject may be a human or a non-human. In other embodiments, the subject is a human. The subject or patient may be undergoing other forms of treatment. In some embodiments, when the subject is a human, the subject does not include any humans who have suffered a cerebrovascular accident (e.g., a stroke).

"Treat," "treating" or "treatment" are each used interchangeably herein to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-analyte (such as cTnI) antibody that differs from the corresponding fragment of anti-analyte (such as cTnI) antibody in amino acid sequence but is still antigenically reactive and can compete with the corresponding fragment of anti-analyte (such as a cTnI) antibody for binding with the analyte (such as cTnI). "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked. One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. Methods of Predicting or Determining Whether a Subject with Coronary Artery Disease is Likely to Experience a Major Adverse Cardiovascular Event In one aspect, the present disclosure relates to methods of predicting or determining whether a subject suffering from coronary artery disease, including, for example, stable coronary artery disease, is likely to experience one or more MACEs. As will be discussed in more detail herein, the methods of the present disclosure involve determining or measuring the concentration or level of cTnI in samples obtained from a subject at multiple time points before as well as during and/or after one or more stress tests and then comparing the concentrations or levels of cTnI determined at these various time points to determine or predict the subject's risk or likelihood of suffering or experiencing one or MACEs.

In one aspect, the methods of the present disclosure involve performing at least one assay to determine one or more levels of cTnI in one or more samples obtained from a subject suffering from CAD, such as stable CAD, prior to the subject undertaking or performing one or more stress tests. In some aspects of the present invention the subjects to be tested are those suffering from CAD, such as stable CAD, and have a high level of cTnI, namely a level of cTnI greater than about 4 pg/mL (namely, a "high risk" subject). Subjects suffering from CAD that have a low baseline level of cTnI, are those that have a cTnI level of less than about 4 pg/mL, less than about 3 pg/mL, less than about 2 pg/mL or about 1 pg/mL. Subjects suffering from CAD that have a low baseline level of cTnI are at a low risk for MACE and do not benefit or require stress testing (namely, a "low risk" subject).

The one or more assays can be performed at any time before the one or more stress tests are conducted as the timing is not critical. For example, the assay can be performed at least two hours before the stress test is conducted, at least one hour before the stress test is conducted, at least 45 minutes before the stress test is conducted, at least 30 minutes before the stress test is conducted, at least 20 minutes before the stress test is conducted, at least 15 minutes before the stress test is conducted, at least 10 minutes before the stress test is conducted, at least 5 minutes before the stress test is conducted, etc.

Additionally, any assay known in the art for determining or measuring the concentration of cTnI in a sample can be used, as the assay type is not critical. For example, an immunoassay (such as a high-sensitivity immunoassay for determining cTnI), a clinical chemistry assay, a point-of-care assay, a single molecule detection assay, or any combinations thereof can be used.

With respect to the stress test used on the subject, the specific type or kind of stress test is not critical.

Either during the stress test and/or after the stress test is completed, one or more additional assays are performed to determine or measure the concentration or level of cTnI in one or more additional samples obtained from the subject. For example, one or more additional assays to measure or determine cTnI levels can be determined at any time during the course or performance of the stress test. For example, the stress test can be stopped or interrupted at any point in time during the duration of the test and one or more assays performed on one or more samples obtained from the subject to determine the concentration or level of cTnI in the sample. Alternatively, or in addition to, one or more additional assays can be performed at any time on one or more samples obtained from the subject after the stress test is completed to determine the concentration(s) or level(s) of cTnI in the samples. For example, one or more assays can be conducted one (1) minute after the stress test is completed, five minutes after the stress test is completed, 10 minutes after the stress test is completed, 15 minutes after the stress test is completed, 20 minutes after the stress test is completed, 25 minutes after the stress test is completed, 30 minutes after the stress test is completed, 45 minutes after the stress test is completed, 60 minutes after the stress test is completed, 90 minutes after the stress test is completed, 2 hours after the stress test is completed, 2.5 hours after the stress test is completed, 3 hours after the stress test is completed, 3.5 hours after the stress test is completed, 4 hours after the stress test is completed, 5 hours after the stress test is completed, 6 hours after the stress test is completed, 7 hours after the stress test is completed, 8 hours after the stress test is completed, 9 hours after the stress test is completed, 10 hours after the stress test is completed, 11 hours after the stress test is completed, 12 hours after the stress test is completed, 13 hours after the stress test is completed, 14 hours after the stress test is completed, 15 hours after the stress test is completed, 16 hours after the stress test is completed, 17 hours after the stress test is completed, 18 hours after the stress test is completed, 19 hours after the stress test is completed, 20 hours after the stress test is completed, 21 hours after the stress test is completed, 22 hours after the stress test is completed, 23 hours after the stress test is completed, 24 hours after the stress test is completed or any combinations thereof.

Once the concentration or level of cTnI is determined in one or more samples obtained during and/or after the stress test, a comparison is made between the level of cTnI obtained before the stress test was conducted with the one or more levels of cTnI obtained during and/or after the stress test and the difference(s) (or "delta(s)") between the measurements determined. For example, if the level of cTnI determined in a sample obtained from a subject before a stress test is 10.0 pg/mL and the level of cTnI determined in a sample obtained from the subject during or after a stress test is 20.0 pg/mL then the difference or delta between the two would be 10 pg/mL. By way of another example, if the level of cTnI determined in a sample obtained from a subject before a stress test is 10.0 pg/mL and the level of cTnI determined in a sample obtained from the subject during a stress test is 30.0 pg/mL, the difference or delta would be 20.0 pg/mL. If a further sample is obtained from the subject after the stress test is completed and the level of cTnI determined in the sample is 40.0 pg/mL, then the difference or delta would be 30.0 pg/mL. In such a situation, there are two deltas, 20.0 pg/mL and 30.0 pg/mL.

Once the difference(s) or delta(s) in cTnI levels is determined, then a determination is made whether or not the subject is likely to experience a MACE. Specifically, a subject is likely to experience a MACE when the difference or delta between the two samples has increased by at least about 10%. Using the above deltas of 20.0 pg/mL and 30.0 pg/mL as examples, a determination or prediction would be made that the subject is likely to or at risk to experience a MACE because the cTnI levels between the two samples had increased more than 10% (namely, greater than 2.0 pg/mL). However, if the deltas were less than 10% (e.g. 1.0 pg/mL), a determination or prediction would be made that the subject not likely to or at risk to experience a MACE (such subjects would be considered to be low risk).

In alternative embodiments, a subject is determined or predicted likely to (i) experience a MACE when the difference or delta has increased by at least about at least about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%; or (ii) not likely to experience a MACE if the difference or delta has not increased by at least about 11%, about 12%, 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%. Interesting, it has been discovered that baseline and serial deltas are more predictive of MACE events than stress tests.

In yet some other embodiments, a subject is determined or predicted likely to (i) experience a MACE when the difference or delta has increased by at least about at least about 20% or (ii) not likely to experience a MACE if the difference or delta has not increased by at least about 20% (such a subject having a difference or delta less than 20% is considered to be low risk for a MACE). Interesting, it has been discovered that baseline and serial deltas are more predictive of MACE events than stress tests.

In situations where it is determined or predicted that a subject is likely to experience at least one MACE, the subject can be treated with one or more therapies to try and prevent the MACE. Specifically, the subject can be administered a therapeutically effective amount of at least one statin, at least one β-blocker, at least one nitrate, at least one phosphodiesterase (PDE) inhibitor, at least one calcium channel blocker, at least one cGMP stimulator, at least one sinus node inhibitor, at least one Rho kinase inhibitor, arginine, allopurinol, testosterone, or any combinations thereof. The types and amounts of therapies can be determined by one skilled in the art.

3. Assays

As mentioned previously herein, any assays known in the art can be used in the methods described herein for determining the level or concentration of cTnI in a sample. Examples of assays that can be used include, but are not limited to, an immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, clinical chemistry assay single molecule detection assay, etc.

a. Immunoassay

The analyte of interest, and/or peptides of fragments thereof (e.g., cTnI), may be analyzed using cTnI antibodies in an immunoassay. The presence or amount of analyte (e.g., cTnI) can be determined using antibodies and detecting specific binding to the analyte (e.g., cTnI). For example, the antibody, or antibody fragment thereof, may specifically bind to the analyte (e.g., cTnI). If desired, one or more of the antibodies can be used in combination with one or more commercially available monoclonal/polyclonal antibodies. Such antibodies are available from companies such as R&D Systems, Inc. (Minneapolis, Minn.) and Enzo Life Sciences International, Inc. (Plymouth Meeting, Pa.).

The presence or amount of analyte (e.g., cTnI) present in a body sample may be readily determined using an immunoassay, such as sandwich immunoassay (e.g., monoclonal-monoclonal sandwich immunoassays, monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)). An example of a point-of-care device that can be used is i-STAT® (Abbott, Laboratories, Abbott Park, Ill.). Other methods that can be used include a chemiluminescent microparticle immunoassay, in particular one employing the ARCHITECT® automated analyzer (Abbott Laboratories, Abbott Park, Ill.), as an example. Other methods include, for example, mass spectrometry, and immunohistochemistry (e.g., with sections from tissue biopsies), using anti-analyte (e.g., anti-cTnI) antibodies (monoclonal, polyclonal, chimeric, humanized, human, etc.) or antibody fragments thereof against analyte (e.g., cTnI). Other methods of detection include those described in, for example, U.S. Pat. Nos. 6,143,576; 6,113, 855; 6,019,944; 5,985,579; 5,947,124; 5,939,272; 5,922, 615; 5,885,527; 5,851,776; 5,824,799; 5,679,526; 5,525, 524; and 5,480,792, each of which is hereby incorporated by reference in its entirety. Specific immunological binding of the antibody to the analyte (e.g., cTnI) can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

A homogeneous format may be used. For example, after the test sample is obtained from a subject, a mixture is prepared. The mixture contains the test sample being assessed for analyte (e.g., cTnI), a first specific binding partner, and a second specific binding partner. The order in which the test sample, the first specific binding partner, and the second specific binding partner are added to form the mixture is not critical. The test sample is simultaneously contacted with the first specific binding partner and the second specific binding partner. In some embodiments, the first specific binding partner and any cTnI contained in the test sample may form a first specific binding partner-analyte (e.g., cTnI)-antigen complex and the second specific binding partner may form a first specific binding partner-analyte of interest (e.g., cTnI)-second specific binding partner complex. In some embodiments, the second specific binding partner and any cTnI contained in the test sample may form a second specific binding partner-analyte (e.g., cTnI)-antigen complex and the first specific binding partner may form a first specific binding partner-analyte of interest (e.g., cTnI)-second specific binding partner complex.

A heterogeneous format may be used. For example, after the test sample is obtained from a subject, a first mixture is prepared. The mixture contains the test sample being assessed for analyte (e.g., cTnI) and a first specific binding partner, wherein the first specific binding partner and any cTnI contained in the test sample form a first specific binding partner-analyte (e.g., cTnI)-antigen complex. The order in which the test sample and the first specific binding partner are added to form the mixture is not critical.

The first specific binding partner may be immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip. In those embodiments where the solid phase is a bead, the bead may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, and NiO/Fe. Examples of ferrimagnetic materials include $NiFe_2O_4$, $CoFe_2O_4$, $Fe_3O_4$ (or $FeO.Fe_2O_3$). Beads can have a solid core portion that is magnetic and is surrounded by one or more non-magnetic layers. Alternately, the magnetic portion can be a layer around a non-magnetic core. The solid support on which the first specific binding member is immobilized may be stored in dry form or in a liquid. The magnetic beads may be subjected to a magnetic field prior to or after contacting with the sample with a magnetic bead on which the first specific binding member is immobilized.

After the mixture containing the first specific binding partner-analyte (e.g., cTnI) antigen complex is formed, any unbound analyte (e.g., CTnI) is removed from the complex using any technique known in the art. For example, the unbound analyte (e.g., cTnI) can be removed by washing. Desirably, however, the first specific binding partner is present in excess of any analyte (e.g., cTnI) present in the test sample, such that all analyte (e.g., cTnI) that is present in the test sample is bound by the first specific binding partner.

After any unbound analyte (e.g., cTnI) is removed, a second specific binding partner is added to the mixture to form a first specific binding partner-analyte of interest (e.g., cTnI)-second specific binding partner complex. Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles (such as a magnetic bead), latex particles or modified surface latex particles, polymer or polymer film, plastic or plastic film, planar substrate, the surface of an assay plate (such as microtiter wells), pieces of a solid substrate material, and the like. An assay strip can be prepared by coating the antibody or plurality of antibodies in an array on a solid support. This strip can then be dipped into the test sample and processed quickly through washes and detection steps to generate a measurable signal, such as a colored spot.

(1) Sandwich Immunoassay

A sandwich immunoassay measures the amount of antigen between two layers of antibodies (i.e., at least one capture antibody) and a detection antibody (i.e., at least one detection antibody). The capture antibody and the detection antibody bind to different epitopes on the antigen, e.g., analyte of interest such as cTnI. Desirably, binding of the capture antibody to an epitope does not interfere with binding of the detection antibody to an epitope. Either monoclonal or polyclonal antibodies may be used as the capture and detection antibodies in the sandwich immunoassay.

Generally, at least two antibodies are employed to separate and quantify analyte (e.g., cTnI) in a test sample. More specifically, the at least two antibodies bind to certain epitopes of analyte (e.g., cTnI) forming an immune complex which is referred to as a "sandwich". One or more antibodies can be used to capture the analyte (e.g., cTnI) in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing analyte (e.g., cTnI) do not bind to all or part of an epitope recognized by the second or subsequent antibodies, thereby interfering with the ability of the one or more second detection antibodies to bind to the analyte (e.g., cTnI).

The antibodies may be used as a first antibody in said immunoassay. The antibody immunospecifically binds to epitopes on analyte (e.g., cTnI). In addition to the antibodies of the present disclosure, said immunoassay may comprise a second antibody that immunospecifically binds to epitopes that are not recognized or bound by the first antibody.

A test sample suspected of containing analyte (e.g., cTnI) can be contacted with at least one first capture antibody (or antibodies) and at least one second detection antibodies either simultaneously or sequentially. In the sandwich assay format, a test sample suspected of containing analyte (e.g., cTnI) is first brought into contact with the at least one first capture antibody that specifically binds to a particular epitope under conditions which allow the formation of a first antibody-analyte (e.g., cTnI) antigen complex. If more than one capture antibody is used, a first multiple capture antibody-cTnI antigen complex is formed. In a sandwich assay, the antibodies, preferably, the at least one capture antibody, are used in molar excess amounts of the maximum amount of analyte (e.g., cTnI) expected in the test sample. For example, from about 5 μg/mL to about 1 mg/mL of antibody per ml of microparticle coating buffer may be used.

i. Anti-cTnI Capture Antibodies

Optionally, prior to contacting the test sample with the at least one first capture antibody, the at least one first capture antibody can be bound to a solid support which facilitates the separation the first antibody-analyte (e.g., cTnI) complex from the test sample. Any solid support known in the art can be used, including but not limited to, solid supports made out of polymeric materials in the forms of wells, tubes, or beads (such as a microparticle). The antibody (or antibodies) can be bound to the solid support by adsorption, by covalent bonding using a chemical coupling agent or by other means known in the art, provided that such binding does not interfere with the ability of the antibody to bind analyte (e.g., cTnI). Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing analyte (e.g., cTnI) is incubated in order to allow for the formation of a first capture antibody (or multiple antibody)-analyte (e.g., cTnI) complex. The incubation can be carried out at a pH of from about 4.5 to about 10.0, at a temperature of from about 2° C. to about 45° C., and for a period from at least about one (1) minute to about eighteen (18) hours, from about 2-6 minutes, from about 7-12 minutes, from about 5-15 minutes, or from about 3-4 minutes.

ii. Detection Antibody

After formation of the first/multiple capture antibody-analyte (e.g., cTnI) complex, the complex is then contacted with at least one second detection antibody (under conditions that allow for the formation of a first/multiple antibody-analyte (e.g., cTnI) antigen-second antibody complex). In some embodiments, the test sample is contacted with the detection antibody simultaneously with the capture antibody. If the first antibody-analyte (e.g., cTnI) complex is contacted with more than one detection antibody, then a first/multiple capture antibody-analyte (e.g., cTnI)-multiple antibody detection complex is formed. As with first antibody, when the at least second (and subsequent) antibody is brought into contact with the first antibody-analyte (e.g., cTnI) complex, a period of incubation under conditions similar to those described above is required for the formation of the first/multiple antibody-analyte (e.g., cTnI)-second/multiple antibody complex. Preferably, at least one second antibody contains a detectable label. The detectable label can be bound to the at least one second antibody prior to, simultaneously with or after the formation of the first/multiple antibody-analyte (e.g., cTnI)-second/multiple antibody complex. Any detectable label known in the art can be used.

Chemiluminescent assays can be performed in accordance with the methods described in Adamczyk et al., *Anal. Chim. Acta* 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-antigen (e.g., cTnI) complexes form. Alternatively, if a second specific binding partner is used and the second specific binding partner is detectably labeled with an acridinium compound, detectably labeled first specific binding partner-analyte (e.g., cTnI)-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of analyte (e.g., cTnI) is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample. Other labels other than chemiluminescent labels can be employed. For instance, enzymatic labels (including but not limited to alkaline phosphatase) can be employed.

The chemiluminescent signal, or other signal, that is generated can be detected using routine techniques known to those skilled in the art. Based on the intensity of the signal generated, the amount of analyte of interest (e.g., cTnI) in the sample can be quantified. Specifically, the amount of analyte (e.g., cTnI) in the sample is proportional to the intensity of the signal generated. The amount of analyte (e.g., cTnI) present can be quantified by comparing the amount of light generated to a standard curve for analyte (e.g., cTnI) or by comparison to a reference standard. The standard curve can be generated using serial dilutions or solutions of known concentrations of analyte (e.g., cTnI) by mass spectroscopy, gravimetric methods, and other techniques known in the art. Quantitation for panel assays, and for multiplex assays likewise has been described in the scientific literature and is known to those skilled in the art.

(2) Forward Competitive Inhibition Assay

In a forward competitive format, an aliquot of labeled analyte of interest (e.g., analyte (e.g., cTnI) having a fluorescent label, a tag attached with a cleavable linker, etc.) of a known concentration is used to compete with analyte of interest (e.g., cTnI) in a test sample for binding to analyte of interest antibody (e.g., cTnI antibody).

In a forward competition assay, an immobilized specific binding partner (such as an antibody) can either be sequentially or simultaneously contacted with the test sample and a labeled analyte of interest, analyte of interest fragment or analyte of interest variant thereof. The analyte of interest peptide, analyte of interest fragment or analyte of interest variant can be labeled with any detectable label, including a detectable label comprised of tag attached with a cleavable linker. In this assay, the antibody can be immobilized on to a solid support. Alternatively, the antibody can be coupled to an antibody, such as an anti-species antibody, that has been immobilized on a solid support, such as a microparticle or planar substrate.

The labeled analyte of interest, the test sample and the antibody are incubated under conditions similar to those described above in connection with the sandwich assay format. Two or more different species of antibody-analyte of interest complexes may then be generated. Specifically, one of the antibody-analyte of interest complexes generated contains a detectable label (e.g., a fluorescent label, etc.) while the other antibody-analyte of interest complex does not contain a detectable label. The antibody-analyte of interest complex can be, but does not have to be, separated from the remainder of the test sample prior to quantification of the detectable label. Regardless of whether the antibody-analyte of interest complex is separated from the remainder of the test sample, the amount of detectable label in the antibody-analyte of interest complex is then quantified. The concentration of analyte of interest (such as membrane-associated analyte of interest, soluble analyte of interest, fragments of soluble analyte of interest, variants of analyte of interest (membrane-associated or soluble analyte of interest) or any combinations thereof) in the test sample can then be determined, e.g., as described above.

(3) Reverse Competitive Inhibition Assay

In a reverse competition assay, an immobilized analyte of interest (e.g., cTnI) can either be sequentially or simultaneously contacted with a test sample and at least one labeled antibody.

The analyte of interest can be bound to a solid support, such as the solid supports discussed above in connection with the sandwich assay format.

The immobilized analyte of interest, test sample and at least one labeled antibody are incubated under conditions similar to those described above in connection with the sandwich assay format. Two different species analyte of interest-antibody complexes are then generated. Specifically, one of the analyte of interest-antibody complexes generated is immobilized and contains a detectable label (e.g., a fluorescent label, etc.) while the other analyte of interest-antibody complex is not immobilized and contains a detectable label. The non-immobilized analyte of interest-antibody complex and the remainder of the test sample are removed from the presence of the immobilized analyte of interest-antibody complex through techniques known in the art, such as washing. Once the non-immobilized analyte of interest antibody complex is removed, the amount of detectable label in the immobilized analyte of interest-antibody complex is then quantified following cleavage of the tag. The concentration of analyte of interest in the test sample can then be determined by comparing the quantity of detectable label as described above.

(4) One-Step Immunoassay or "Capture on the Fly" Assay

In a capture on the fly immunoassay, a solid substrate is pre-coated with an immobilization agent. The capture agent, the analyte (e.g., cTnI) and the detection agent are added to the solid substrate together, followed by a wash step prior to detection. The capture agent can bind the analyte (e.g., cTnI) and comprises a ligand for an immobilization agent. The capture agent and the detection agents may be antibodies or any other moiety capable of capture or detection as described herein or known in the art. The ligand may comprise a peptide tag and an immobilization agent may comprise an anti-peptide tag antibody. Alternately, the ligand and the immobilization agent may be any pair of agents capable of binding together so as to be employed for a capture on the fly assay (e.g., specific binding pair, and others such as are known in the art). More than one analyte may be measured. In some embodiments, the solid substrate may be coated with an antigen and the analyte to be analyzed is an antibody.

In certain other embodiments, in a one-step immunoassay or "capture on the fly", a solid support (such as a microparticle) pre-coated with an immobilization agent (such as biotin, streptavidin, etc.) and at least a first specific binding member and a second specific binding member (which function as capture and detection reagents, respectively) are used. The first specific binding member comprises a ligand for the immobilization agent (for example, if the immobilization agent on the solid support is streptavidin, the ligand on the first specific binding member may be biotin) and also binds to the analyte of interest (e.g., cTnI). The second specific binding member comprises a detectable label and binds to an analyte of interest (e.g., cTnI). The solid support and the first and second specific binding members may be added to a test sample (either sequentially or simultaneously). The ligand on the first specific binding member binds to the immobilization agent on the solid support to form a solid support/first specific binding member complex. Any analyte of interest present in the sample binds to the solid support/first specific binding member complex to form a solid support/first specific binding member/analyte complex. The second specific binding member binds to the solid support/first specific binding member/analyte complex and the detectable label is detected. An optional wash step may be employed before the detection. In certain embodiments, in a one-step assay more than one analyte may be measured. In certain other embodiments, more than two specific binding members can be employed. In certain other embodiments, multiple detectable labels can be added. In certain other embodiments, multiple analytes of interest can be detected, or their amounts, levels or concentrations, measured, determined or assessed.

The use of a capture on the fly assay can be done in a variety of formats as described herein, and known in the art. For example, the format can be a sandwich assay such as described above, but alternately can be a competition assay, can employ a single specific binding member, or use other variations such as are known.

(5) Single Molecule Detection Assay

Single molecule detection assays and methods, such as the use of a nanopore device or nanowell device, can also be used. Examples of nanopore devices are described in International Patent Publication No. WO 2016/161402, which is hereby incorporated by reference in its entirety. Examples of nanowell device are described in International Patent Publication No. WO 2016/161400, which is hereby incorporated by reference in its entirety. Other devices and methods appropriate for single molecule detection can also be employed.

4. Sample, Test Sample or Biological Sample

As used herein, "sample", "test sample", "biological sample" refer to fluid sample containing or suspected of containing cTnI. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing cTnI may be assayed directly. In a particular example, the source containing cTnI is a human bodily substance (e.g., bodily fluid, blood such as whole blood, serum, plasma, urine, saliva, sweat, sputum, semen, mucus, lacrimal fluid, lymph fluid, amniotic fluid, interstitial fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis.

A wide range of volumes of the fluid sample may be analyzed. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL.

In some cases, the fluid sample may be diluted prior to use in an assay. For example, in embodiments where the source containing cTnI is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source containing cTnI is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

5. Controls

It may be desirable to include a control (such as a positive and/or negative control, which are well known in the art). The control may be analyzed concurrently with the sample from the subject as described above. The results obtained from the subject sample can be compared to the results or information obtained from the control. Standard curves may be provided, with which assay results for the sample may be compared. Such standard curves present levels of marker as a function of assay units, i.e., fluorescent signal intensity, if a fluorescent label is used. Using samples taken from multiple donors, standard curves can be provided for reference levels of cTnI in normal healthy subjects, as well as for subjects suffering from CAD, such as, for example, stable CAD.

6. Kit

Provided herein is a kit, which may be used in the methods described herein for assaying or assessing a sample for cTnI or a fragment thereof. The kit comprises at least one component for assaying the test sample for cTnI instructions for assaying the test sample for cTnI. For example, the kit can comprise instructions for assaying the test sample for cTnI by immunoassay, e.g., chemiluminescent microparticle immunoassay. Instructions included in kits can be affixed to packaging material or can be included as a package insert, or can be viewed or downloaded from a particular website that is recited as part of the kit packaging or inserted materials. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to cTnI. The antibody may be a cTnI capture antibody and/or a cTnI detection antibody.

Alternatively or additionally, the kit can comprise a calibrator or control, as described above, e.g., purified, and optionally lyophilized, cTnI, and/or at least one container (e.g., tube, microtiter plates or strips, which can be already coated with an anti-cTnI monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve.

The kit may further comprise reference standards for quantifying cTnI. The reference standards may be employed to establish standard curves for interpolation and/or extrapolation of cTnI concentrations. The reference standards may include a high cTnI concentration level, for example, about 100000 pg/mL, about 125000 pg/mL, about 150000 pg/mL, about 175000 pg/mL, about 200000 pg/mL, about 225000 pg/mL, about 250000 pg/mL, about 275000 pg/mL, or about 300000 pg/mL; a medium cTnI concentration level, for example, about 25000 pg/mL, about 40000 pg/mL, about 45000 pg/mL, about 50000 pg/mL, about 55000 pg/mL, about 60000 pg/mL, about 75000 pg/mL or about 100000 pg/mL; and/or a low cTnI concentration level, for example, about 1 pg/mL, about 5 pg/mL, about 10 pg/mL, about 12.5 pg/mL, about 15 pg/mL, about 20 pg/mL, about 25 pg/mL, about 30 pg/mL, about 35 pg/mL, about 40 pg/mL, about 45 pg/mL, about 50 pg/mL, about 55 pg/mL, about 60 pg/mL, about 65 pg/mL, about 70 pg/mL, about 75 pg/mL, about 80 pg/mL, about 85 pg/mL, about 90 pg/mL, about 95 pg/mL, or about 100 pg/mL.

Any antibodies, which are provided in the kit, such as recombinant antibodies specific for cTnI, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes (e.g., cTnI) or reagents for detecting the analyte (e.g., cTnI). The antibodies, calibrators, and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays, The kit can also optionally include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, whole blood, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of traumatic brain injury or disorder.

7. Adaptation of Kit and Method

The kit (or components thereof), as well as the method for assessing or determining the concentration of cTnI in a test sample using an assay as described herein, can be adapted for use in a variety of automated and semi-automated systems (including those wherein the solid phase comprises a microparticle), as described, e.g., U.S. Pat. No. 5,063,081, U.S. Patent Application Publication Nos. 2003/0170881, 2004/0018577, 2005/0054078, and 2006/0160164 and as commercially marketed e.g., by Abbott Laboratories (Abbott Park, Ill.) as Abbott Point of Care (i-STAT® or i-STAT Alinity, Abbott Laboratories) as well as those described in U.S. Pat. Nos. 5,089,424 and 5,006,309, and as commercially marketed, e.g., by Abbott Laboratories (Abbott Park, Ill.) as ARCHITECT® or the series of Abbott Alinity devices.

Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits, and kit components can be employed in other formats, for example, on electrochemical or other hand-held or point-of-care assay systems. As mentioned previously, the present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. No. 5,063,081, U.S. Patent App. Publication Nos. 2003/0170881, 2004/0018577, 2005/0054078, and 2006/0160164, which are incorporated in their entireties by reference for their teachings regarding same.

In particular, with regard to the adaptation of an assay to the i-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an i-STAT® cartridge with a fluidics format suitable for immunoassay. On a portion of the silicon chip, there is a specific binding partner for cTnI, such as one or more cTnI antibodies (one or more monoclonal/polyclonal antibody or a fragment thereof, a variant thereof, or a fragment of a variant thereof that can bind cTnI) or one or more anti-cTnI DVD-Igs (or a fragment thereof, a variant thereof, or a fragment of a variant thereof that can bind cTnI), either of which can be detectably labeled. Within the fluid pouch of the cartridge is an aqueous reagent that includes p-aminophenol phosphate.

In operation, a sample from a subject with CAD is added to the holding chamber of the test cartridge, and the cartridge is inserted into the i-STAT® reader. A pump element within the cartridge pushes the sample into a conduit containing the chip. The sample is brought into contact with the sensors allowing the enzyme conjugate to dissolve into the sample. The sample is oscillated across the sensors to promote formation of the sandwich of approximately 2-12 minutes. In the penultimate step of the assay, the sample is pushed into a waste chamber and wash fluid, containing a substrate for the alkaline phosphatase enzyme, is used to wash excess enzyme conjugate and sample off the sensor chip. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of cTnI in the sample by means of an embedded algorithm and factory-determined calibration curve. Adaptation of a cartridge for multiplex use, such as used for i-Stat, has been described in the patent literature, such as for example, U.S. Pat. No. 6,438,498, the contents of which are herein incorporated by reference.

The methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, improved signal generation may be obtained, e.g., in an i-STAT® cartridge format, using a nucleic acid sequence linked to the signal antibody as a signal amplifier.

While certain embodiments herein are advantageous when employed to assess disease, such as traumatic brain injury, the assays and kits also optionally can be employed to assess cTnI in other diseases, disorders, and conditions as appropriate.

8. Example

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following example, which is merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

EXAMPLE

This example describes a study to determine the likelihood of a major adverse cardiovascular event (MACE) in coronary artery disease (CAD) patients by measuring cardiac troponin I (cTnI) levels before and after stress testing.

METHODS

Study Sample

Patients were enrolled into the MIPS (Mental Stress Ischemia Prognosis Study), a prospective study that recruited patients with stable CAD between Jun. 23, 2011 and Aug. 5, 2014 at Emory University-affiliated hospitals. Presence of CAD was defined by an abnormal coronary angiogram demonstrating evidence of atherosclerosis with at least luminal irregularities, documented previous percutaneous or surgical coronary revascularization, documented myocardial infarction, or a positive nuclear stress test. Patients with acute coronary syndrome or decompensated heart failure during the previous 2 months, end-stage renal disease, or unstable psychiatric conditions were excluded. Clinical information including previous CAD events, CAD risk factors, coronary angiography results, and current medications were documented using standardized questionnaires and chart reviews. The research protocol was approved by the institutional review board of Emory University and all participants provided informed consent. Patients were tested in the morning after a 12 hour fast as described previously (Ramadan et al., J Am Heart Assoc., 2(5):e000321 (2013)). Antianginal medications (beta-blockers, calcium-channel blockers, and long-acting nitrates), xanthine derivatives, and caffeine-containing products were withheld for 24 hours prior to stress testing (conventional and mental). Estimated creatinine clearance was calculated by means of the Chronic Kidney Disease Epidemiology Collaboration equation. Angiographic CAD severity was calculated using the Gensini score with a median time between the angiogram and enrollment of 2.1 years (interquartile range [IQR]: 1.0 to 4.7 years) (Ramadan et al., supra).

Myocardial Perfusion Imaging and SPECT Images Interpretation

Myocardial perfusion imaging with technetium Tc 99m sestamibi-single-photon emission computed tomography (SPECT) was performed at rest and 60 minutes after physical stress according to standard protocols (Ramadan et al., supra). Studies were interpreted by two experienced readers without prior knowledge of severity of CAD or other patient medical history. Discrepancies in interpretation of SPECT images were resolved by consensus. Rest and stress images were visually compared for number and severity of perfusion defects using a 17-segment model. Each segment was scored from 0 to 4, with 0 being normal uptake and 4 no uptake. Ischemia was defined as a new impairment with a score $\geq 2$ in any segment, or as worsening of a pre-existing impairment by at least 2 points if in a single segment, or by at least 1 point if in 2 or more contiguous segments (Holly et al., J Nucl Cardiol., 17(5): 941-73 (2010)). In addition to individual segment scores, summed scores were calculated in a conventional fashion, including a summed stress score, a summed rest score, and a summed difference score, the latter representing a semi-quantitative measure of inducible ischemia (Holly et al., supra). The percentage of myocardium with resting perfusion defects was calculated as: (summed rest score+68)×100, and percent of ischemic myocardium was calculated as: (summed difference score+68)×100 (Vaccarino et al., J Am Heart Assoc., 5(9): (2016)). Only a limited number of patients had an echocardiogram performed within one year of enrollment, thus ejection fraction was evaluated using SPECT imaging from the resting scan.

Hs-cTnI Assay

Patients had fasting venous blood drawn at rest and 45 minutes after exercise stress testing (n=365). Samples were processed and stored at −80° C. Plasma hs-cTnI was measured using the ARCHITECT STAT Hs-cTnI assay (Abbott Laboratories, Abbott Park, Ill.), which has a limit of detection of 1.2 pg/ml and an interassay coefficient of variation of <10% at 4.7 pg/ml. The upper reference limit (99th centile) ranges between 24 pg/ml and 30 pg/ml in healthy populations (Apple et al., Clin Chem., 58(11):1574-81 (2012); Keller et al., JAMA, 306(24): 2684-93 (2011); and Zeller et al., Eur Heart J., 35(5): 271-81 (2014)), with a sex-specific upper reference range of 36 pg/ml for men and 15 pg/ml for women (Aw et al., Clin Chim Acta., 422: 26-8 (2013)).

Long-Term Follow-Up

Adjudicated events (cardiovascular death, myocardial infarction, and unstable angina with coronary revascularization) were ascertained after enrollment. Mortality data were collected during follow-up visits at one and two years, phone calls at three years, medical records review, and queries from the Social Security Death Index. The primary end point of follow-up was a combined outcome of major adverse cardiovascular events (MACE) including cardiovascular death, myocardial infarction, and unstable angina with coronary revascularization. Cardiovascular death was defined as death attributable to an ischemic cardiovascular cause (fatal myocardial infarction), cardiac arrhythmia (including resuscitated), congestive heart failure, or a cardiac procedure (coronary artery bypass grafting or angioplasty). All events identified were adjudicated by study investigators who were blinded to the stress test data.

Statistical Analyses

Descriptive data were summarized as mean±standard deviation (SD) for continuous variables and as percentages for categorical variables. Two-sample Student's t test and Kruskal-Wallis tests for continuous variables and chi-square tests for categorical variables were performed to compare those with <20% versus ≥20% hs-cTnI increase with exercise. The cut-off of 20% increase in hs-cTnI was chosen in accordance with the National Academy of Clinical Biochemistry laboratory medicine practice guidelines which represents a significant (3 SD) change in hs-cTnI level on the basis of a 5%-7% analytical coefficient of variance typical for most assays in the concentration range indicating acute MI (Group et al., Clin Chem. 2007; 53(12):2086-96). The natural logarithmic transformation was used for non-normally distributed variables (resting hs-cTnI and Gensini score). Linear mixed model analysis was used to study factors associated with delta (post-stress minus rest) hs-cTnI level.

To investigate the association between the change in hs-cTnI level with exercise and cardiovascular events, delta hs-cTnI was examined both as a continuous and a dichotomized (below or ≥20% increase) variable in Fine and Gray's (FG) sub-distribution hazard models with non-cardiovascular death treated as competing risk (Gray R. J., The Annals of Statistics. 1988:1141-54). Subjects were also divided with respect to the median resting hs-cTnI level (4 ng/L). Finally, the subjects were divided into four groups based on both the resting and exercise-induced change in hs-cTnI levels: (1) low resting hs-cTnI and <20% hs-cTnI increase with stress; (2) low resting hs-cTnI and ≥20% hs-cTnI increase with stress; (3) high resting hs-cTnI and <20% hs-cTnI response to stress; (4) high resting hs-cTnI and ≥20% hs-cTnI response to stress. Selection of factors to be included in the models was based on prior evidence of an association with hs-cTnI or cardiovascular disease events (Yeboah et al., Circulation. 2009; 120(6):502-9). The covariates retained in the fully adjusted models included demographic factors (age, sex, and race), resting hs-cTnI, exercise-induced ischemia status, lifestyle, and clinical cardiovascular risk factors (smoking, BMI, dyslipidemia, diabetes, hypertension, heart failure [HF], prior MI, creatinine clearance [CrCl], and Gensini score).

The C-statistic and category-free net reclassification improvement (NRI), as well as the integrated discrimination improvement (IDI) that can account for censored data were calculated as measures of risk discrimination (Uno et al., Stat Med. 2011; 30(10):1105-17; Uno et al., Stat Med. 2013; 32(14):2430-42; Pencina et al., Stat Med. 2008; 27(2):157-72; discussion 207-12; and Pencina et al., Stat Med. 2011; 30(1):11-21). The significance level for both main effects and interactions was set at p<0.05. All statistical analyses were conducted using SAS version 9.4 (SAS Institute, Cary, N.C.).

Results

Of 365 patients with stable CAD, 30% (n=110) had exercise-induced myocardial ischemia. The sample mean age (±SD) was 62±9 years, 77% were men, and 25% black. The median levels for resting, post-stress and delta (post-stress minus pre-stress) hs-cTnI were 4.0 pg/ml (IQR: 2.6 to 6.3 pg/ml), 3.80 pg/ml (IQR: 2.5 to 6.3 pg/ml) and 0 pg/ml (IQR: −0.6 to 0.6 pg/ml), respectively. Overall, 97 (27%) patients had a ≥20% increase in hs-cTnI level in response to exercise stress testing. Patients with ≥20% increase in hs-cTnI with stress compared with those with <20% increase shared similar clinical characteristics with the exception of the presence of inducible myocardial ischemia (41% vs. 28%, p=0.03, respectively). The patient characteristics are set forth in Table 1.

TABLE 1

Characteristics of the Study Population by High-sensitivity Cardiac Troponin I (hs-cTnI) Response to Exercise Stress Testing.

| | | hs-cTnI Response | | |
| --- | --- | --- | --- | --- |
| | Total | Low (<20%) | High (≥20%) | p-value |
| Total Demographics, n | 365 | 268 | 97 | |
| Age, Years, Mean (SD) | 62 (9) | 62 (9) | 63 (9) | 0.29 |
| Male, n (%) | 282 (77) | 216 (81) | 72 (74) | 0.28 |
| Black race, n (%) | 92 (25) | 64 (24) | 21 (22) | 0.87 |
| Medical History and CAD Risk Factors | | | | |
| Current Smoking, n (%) | 39 (11) | 27 (10) | 9 (9) | 0.94 |
| Diabetes, n (%) | 100 (28) | 71 (27) | 27 (28) | 0.76 |
| Hypertension, n (%) | 272 (75) | 198 (74) | 74 (76) | 0.87 |
| Dyslipidemia, n (%) | 300 (83) | 218 (82) | 81 (84) | 0.75 |
| BMI, kg/m², Mean (SD) | 39 (5) | 29 (5) | 30 (4) | 0.24 |
| Prior MI, n (%) | 141 (39) | 112 (42) | 28 (29) | 0.07 |
| Heart Failure, n (%) | 50 (14) | 42 (16) | 9 (9) | 0.17 |
| Prior Revascularization, n (%) | 198 (55) | 59 (157) | 46 (47) | 0.10 |
| Gensini score, Median (IQR) | 23 (42) | 23 (41) | 22 (43) | 0.92 |
| CrCl, ml/min per 1.73 m² | 80 (18) | 79 (17) | 83 (20) | 0.08 |
| Ejection Fraction, %, Mean (SD) | 55 (11) | 54 (9) | 56 (11) | 0.16 |
| Inducible Ischemia, n (%) | 110 (30) | 73 (28) | 39 (41) | 0.03 |
| Baseline hs-cTnI, ng/L, Median (IQR) | 4.0 (4) | 4.0 (4) | 3.5 (3) | 0.49 |

TABLE 1-continued

Characteristics of the Study Population by High-sensitivity Cardiac Troponin I (hs-cTnI) Response to Exercise Stress Testing.

| | | hs-cTnI Response | | |
|---|---|---|---|---|
| | Total | Low (<20%) | High (≥20%) | p-value |
| Medications | | | | |
| Aspirin, n (%) | 319 (88) | 239 (90) | 83 (86) | 0.51 |
| Beta-Blocker, n (%) | 257 (71) | 191 (72) | 68 (70) | 0.76 |
| ACE Inhibitors, n (%) | 173 (48) | 128 (48) | 47 (48) | 0.94 |
| Statin use, n (%) | 322 (89) | 239 (90) | 82 (85) | 0.23 |

Abbreviations - Hs-cTnI: High-sensitivity Cardiac Troponin I; BMI: Body Mass Index; MI: Myocardial Infarction; CrCl: Creatinine Clearance; ACE: Angiotensin Converting Enzyme.
*Statistical tests - categorical variables: chi-square or Fisher's exact test; continuous variables: Student t test or Wilcoxon-Mann-Whitney U test, when appropriate.

During exercise stress testing, compared to patients with <20% increase in hs-cTnI, those with ≥20% hs-cTnI in response to exercise demonstrated a significantly higher post-stress systolic blood pressure (159 vs. 166 mmHg, p=0.05) and more myocardial perfusion defects (summed stress percent, 9.3% vs. 11.7%, p=0.03), as shown in Table 2.

TABLE 2

Hemodynamic Responses and Perfusion Defects with Exercise Stress Testing

| | hs-cTnI Response to Exercise | | |
|---|---|---|---|
| | Low (<20% increase) Mean (SD) | High (≥20% increase) Mean (SD) | P-value |
| Systolic Blood Pressure (mmHg) | | | |
| Rest | 137 (18) | 138 (19) | 0.70 |
| Post-stress | 159 (20) | 166 (23) | 0.05 |
| Systolic Blood Pressure Reactivity | 22 (20) | 26 (21) | 0.08 |
| Heart Rate (bmp) | | | |
| Rest | 66 (11) | 65 (12) | 0.82 |
| Post-stress | 116 (14) | 117 (14) | 0.46 |
| Heart Rate Reactivity | 50 (14) | 49 (14) | 0.45 |
| Rate Pressure Product (mmHg*bmp) | | | |
| Rest | 9,020 (2,045) | 9,038 (2,067) | 0.95 |
| Post-stress | 17,952 (4,460) | 18,412 (4,779) | 0.66 |
| Rate Pressure Product Reactivity | 8,941 (4,294) | 9,374 (4,473) | 0.46 |
| Perfusion Defects (% of TV) | | | |
| Summed Rest Percent (SR %) | 8.0 (7.5) | 8.9 (7.9) | 0.29 |
| Summed Stress Percent (SS %) | 9.3 (8.1) | 11.7 (10.1) | 0.03 |
| Summed Difference Percent (SD %) | 3.7 (4.0) | 4.8 (5.1) | 0.05 |

Abbreviations - Hs-cTnI: High-sensitivity Cardiac Troponin I; SD: standard deviation.
*Statistical tests: Student t test or Wilcoxon-Mann-Whitney U test, when appropriate.

In linear mixed model analysis that included CAD risk factors, only the presence of inducible myocardial ischemia was independently associated with a higher increase in hs-cTnI level with stress, as shown in Table 3.

TABLE 3

Associations Between Delta (Post-stress - Rest) High-sensitivity Cardiac Troponin I (hs-cTnI) Levels, Demographic and Clinical Variables Based on Bivariate and Multivariable Analyses

| | Bivariate Analysis | | Multivariate Analysis | |
|---|---|---|---|---|
| Demographic and clinical variables | β (SE) | p-value | β (SE) | p-value |
| Log resting hs-cTnI, per 20% increase | 8.76 (5.83) | 0.03 | −1.18 (0.73) | 0.10 |
| Exercise-induced myocardial ischemia | 6.64 (4.17) | 0.02 | 5.59 (2.73) | 0.01 |
| Age | 0.66 (0.52) | 0.21 | −0.01 (0.09) | 0.92 |
| Male | 7.10 (11.80) | 0.54 | 1.15 (1.94) | 0.55 |
| African American | −7.40 (11.24) | 0.51 | −1.52 (1.98) | 0.44 |
| Previous myocardial infarction | −8.86 (9.78) | 0.36 | −1.50 (1.67) | 0.37 |
| Hypertension | −12.83 (10.97) | 0.38 | −2.95 (1.91) | 0.12 |
| Dyslipidemia | 8.66 (12.53) | 0.49 | 0.09 (0.08) | 0.89 |
| Diabetes | −7.93 (10.77) | 0.46 | −1.68 (1.93) | 0.39 |
| Current smoking | 8.86 (9.61) | 0.36 | −0.01 (1.58) | 0.94 |
| Body mass index | −0.85 (0.91) | 0.34 | 0.13 (0.16) | 0.41 |
| Heart failure | −2.72 (13.63) | 0.84 | 4.93 (3.01) | 0.10 |
| Creatinine clearance, 10 units change | 0.44 (0.27) | 0.11 | 0.07 (0.05) | 0.15 |
| Ejection fractions, 10% change | −0.08 (0.06) | 0.17 | −0.88 (0.68) | 0.19 |
| Log CAD severity score (Gensini) | −6.21 (4.54) | 0.18 | −0.04 (0.11) | 0.70 |

Unstandardized regression coefficients β (SE) reported.
SE: Standard error.

Association Between Adverse Cardiovascular Outcomes and Resting Hs-cTnI Levels

Patients were followed up for a median (interquartile range) period of 3.0 (2.9-3.1) years. A total of 39 patients (11%) had adverse events, including 3 cardiovascular deaths, 11 MIs and 26 unstable angina events followed by revascularization.

In both bivariate and fully adjusted FG models, resting hs-cTnI levels were associated with increased risk for MACE (Table 4, FIG. 1A). In a multivariate model adjusting for inducible ischemia, demographics (age, sex, and race), lifestyle and clinical cardiovascular risk factors (smoking, BMI, dyslipidemia, diabetes, hypertension, HF, prior MI, CrCl, and Gensini score), each 20% increment in the resting hs-cTnI level was associated with an adjusted 9% (sub-distribution hazard ratio [sHR] 1.09, 95% CI 1.03-1.17, p=0.02) increase in the hazard of MACE, as shown in Table 4. When dichotomized by the median resting value of hs-cTn (4 ng/L), those with higher resting levels had worse outcomes compared to those with lower resting levels (sHR 1.66, 95% CI 1.01-2.73, p=−0.04), as shown in FIG. 1A. Other independent predictors of adverse outcomes in the fully adjusted model included creatinine clearance (sHR 1.29, 95% CI 1.01-1.65, p=0.04, per 10 units change) and the presence of exercise-induced myocardial ischemia (sHR 2.18, 95% CI 1.04-4.57, p=0.04).

Figure 1B:
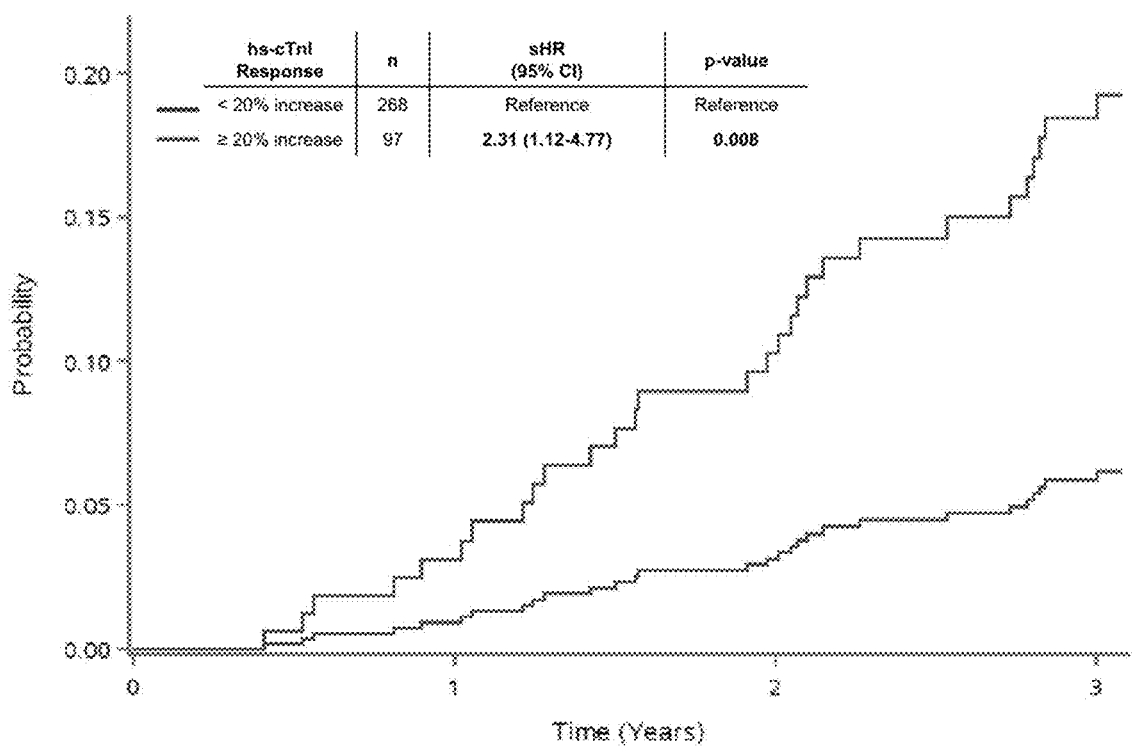

Association Between Adverse Cardiovascular Outcomes and Change in Hs-cTnI Levels with Exercise In both bivariate and fully adjusted FG models, the change (post-stress minus rest) in hs-cTnI levels was associated with increased risk for MACE, as shown in Table 4. After multivariate adjustment for the aforementioned covariates, each 20% increment in the change in hs-cTnI level was associated with an adjusted 15% (sHR 1.15, 95% CI 1.05-1.27, p=0.003) increase in the hazard of MACE, as shown in Table 4. The results were consistent when the hs-cTnI response to the exercise stress test was dichotomized into <20% or ≥20% increase. The presence of 20% hs-cTnI level increase in response to stress was associated with an adjusted sHR of 2.31 (95% CI 1.12-4.77, p=0.008), as shown in FIG. 1B.

TABLE 4

Bivariate and Multivariate Sub-Distribution Hazard Ratios (sHR) and 95% Confidence Intervals (CI) for Major Adverse Cardiovascular Event (MACE) Incidence by Fine & Gray's Proportional Sub-Distribution Hazards Models

|  | Bivariate sHR (95% CI) | p-value | Multivariate sHR (95% CI) | p-value |
|---|---|---|---|---|
| Change in hs-cTnI, per 20% increase | 1.20 (1.06-1.35) | 0.003 | 1.15 (1.05-1.27) | 0.003 |
| Resting hs-cTnI, per 20% increase | 1.12 (1.06-1.19) | <0.001 | 1.09 (1.03-1.17) | 0.02 |
| Inducible myocardial ischemia | 2.40 (1.25-4.60) | 0.009 | 2.18 (1.04-4.57) | 0.04 |
| Age | 0.99 (0.95-1.02) | 0.47 | 1.00 (0.96-1.05) | 0.90 |
| Male | 1.34 (0.59-3.06) | 0.48 | 1.02 (0.98-1.06) | 0.87 |
| African American | 1.42 (0.72-2.80) | 0.32 | 0.99 (0.42-2.34) | 0.97 |
| Previous MI | 1.29 (0.67-2.26) | 0.44 | 1.29 (0.59-2.81) | 0.52 |
| Hypertension | 0.76 (0.38-1.54) | 0.44 | 0.66 (0.29-1.52) | 0.33 |
| Dyslipidemia | 0.74 (0.34-1.62) | 0.45 | 0.61 (0.26-1.46) | 0.27 |
| Diabetes | 1.51 (0.77-2.97) | 0.22 | 1.47 (0.66-3.30) | 0.35 |
| Current smoking | 1.74 (0.87-3.48) | 0.11 | 1.36 (0.65-2.87) | 0.42 |
| BMI, 1 unit change | 1.00 (0.94-1.06) | 0.93 | 0.99 (0.92-1.08) | 0.88 |
| Heart failure | 1.51 (0.66-3.45) | 0.32 | 1.44 (0.57-3.67) | 0.98 |
| Creatinine clearance, 10 units change | 1.27 (1.07-1.51) | 0.006 | 1.29 (1.01-1.65) | 0.04 |
| Log CAD severity score (Gensini) | 1.33 (0.94-1.91) | 0.10 | 1.33 (0.84-1.74) | 0.10 |

Figure 1C:
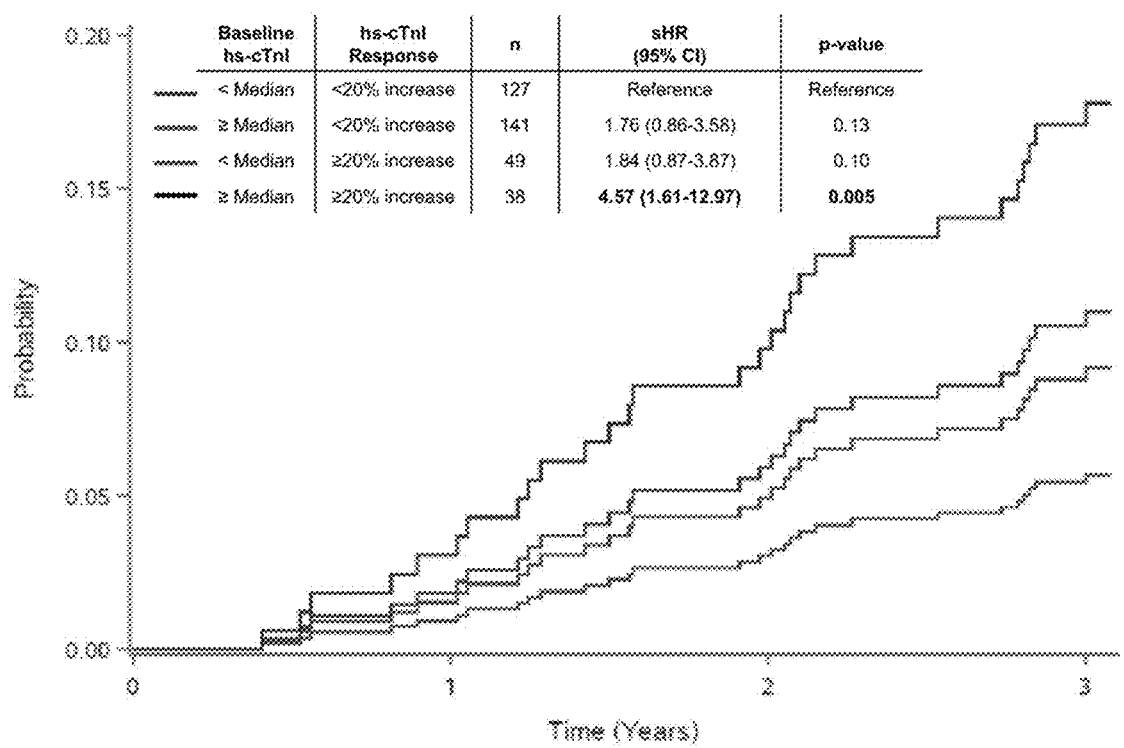

Abbreviations - BMI: Body Mass Index; MI: Myocardial Infarction; CAD: Coronary Artery Disease.
MACE defined as a combination of CV death, MI, and unstable angina with revascularization. sHR represents the risk of endpoints for the comparison versus the reference groups while treating non-cardiovascular death as competing risk. State what the adjustments were for Finally, when subjects were divided into 4 groups based on their resting hs-cTnI levels (below or above median) and its change with exercise (<20% and ≥20% increase), the sub-group with concurrently high resting hs-cTnI level (≥4 ng/L) and ≥20% hs-cTnI level elevation with stress had the greatest increase in the MACE incidence (adjusted sHR 4.57, 95% CI 1.61-12.97, p=0.005) compared with the reference group (low resting hs-cTnI level and <20% increase with stress), as shown in FIG. 1C. The interaction between resting and change in hs-cTnI was not significant (p=0.23).

Risk Prediction Performance

We tested the incremental value of adding the presence of inducible ischemia, resting hs-cTnI level, or delta hs-cTnI level individually and in combination to a model with traditional risk factors and clinical characteristics (including sex, race, age, hypertension, dyslipidemia, prior MI, HF, body mass index, diabetes, smoking history, CrCl and C-reactive protein) for predicting incident MACE. Addition of inducible ischemia status to risk factors significantly improved the C-statistic (from 0.63 to 0.67, p=0.002), as shown in Table 5. Addition of resting hs-cTnI level did not significantly (p=0.08) improve the C-statistic from a model including risk factors and ischemia status, but improved the net reclassification improvement (p=0.01). However, including resting and delta hs-cTnI levels improved the C-statistic from a model with risk factors alone (0.63 to 0.68, p<0.001) or a model with risk factors and ischemia (0.67 to 0.71, p=0.007), as shown in Table 5. There were also simultaneous significant improvements in the continuous net reclassification improvement and integrated discrimination improvement.

The results of this Example demonstrate that, in stable CAD patients, an elevation of hs-cTnI with exercise stress testing in combination with baseline hs-cTnI predicts adverse cardiovascular outcomes beyond traditional cardiovascular risk factors and inducible ischemia diagnosed by myocardial perfusion imaging. The results highlight the importance of the assessment of dynamic changes in hs-cTnI levels instead of its resting levels to improve the risk stratification of subjects with stable CAD. Whether patients with exercise-induced hs-cTnI increase would benefit from intervention requires further investigation.

TABLE 5

Discrimination and Reclassification Improvement of Statistical Models Predicting Major Adverse Cardiovascular Events (MACE) Including High-Sensitivity Troponin I (hs-cTnI) in Combination with Traditional Risk Factors*

|  | C-statistic | | Category-free NRI | | IDI | |
|---|---|---|---|---|---|---|
|  | AUC | p-value | NRI Value | p-value | IDI Value | p-value |
| Model 1: Risk Factors[†] | 0.63 | Reference | Reference | Reference | Reference | Reference |
| Model 1 + Inducible Ischemia | 0.67 | 0.002 | 0.33 | 0.006 | 0.03 | 0.01 |
| Model 1 + Resting hs-cTnI | 0.68 | <0.001 | 0.35 | 0.002 | 0.03 | 0.008 |
| Model 1 + Resting & Change in hs-cTnI | 0.70 | <0.001 | 0.37 | 0.001 | 0.04 | 0.002 |
| Model 2: Risk Factors[†] + Inducible Ischemia | 0.67 | Reference | Reference | Reference | Reference | Reference |
| Model 2 + Resting hs-cTnI | 0.68 | 0.08 | 0.12 | 0.13 | 0.01 | 0.19 |
| Model 2 + Resting & change in hs-cTnI | 0.71 | 0.007 | 0.21 | 0.009 | 0.02 | 0.04 |

Abbreviations - hs-cTnI: high-sensitivity cardiac troponin I; NRI: net reclassification improvement; IDI: integrated discrimination improvement.
MACE defined as a combination of CV death, MI and unstable angina with revascularization.

[†]Traditional Risk Factors: sex, race, age (continuous), hypertension, dyslipidemia, prior MI, HF, body mass index (continuous), diabetes, smoking history, creatinine clearance and C-reactive protein.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

least one nitrate, at least one phosphodiesterase (PDE) inhibitor, at least one calcium channel blocker, at least one cGMP stimulator, at least one sinus node inhibitor, at least one Rho kinase inhibitor, arginine, allopurinol, testosterone, or any combinations thereof.

2. The method of claim 1, wherein the human has stable coronary artery disease.

3. The method of claim 1, wherein the level of cTnI is detected using a high sensitivity cardiac troponin I assay.

4. The method of claim 3, wherein the high sensitivity cardiac troponin I assay is an immunoassay, a clinical

---

---

What is claimed is:

1. A method comprising:
   (a) detecting a resting level of cardiac troponin I (cTnI) of at least 4 ng/mL in a blood, serum, or plasma sample obtained from a human with coronary artery disease (CAD),
   (b) detecting the level of cTnI in a blood, serum, or plasma sample obtained from the human during or after exercise,
   (c) measuring at least a 10% increase in the cTnI level during or after exercise as compared the resting cTnI level, which indicates that the human is likely to experience a major adverse cardiovascular event (MACE), and
   (d) administering to the human a therapeutically effective amount of at least one statin, at least one β-blocker, at chemistry assay, a point-of-care assay, or a single molecule detection assay.

5. The method of claim 1, wherein (b) comprises detecting the level of cTnI in a sample obtained from the human during exercise.

6. The method of claim 1, wherein (b) comprises detecting the level of cTnI in a sample obtained from the human after exercise.

7. The method of claim 6, wherein the sample is obtained from the human about 45 minutes after exercise.

8. The method of claim 1, wherein the human has exercise-induced myocardial ischemia.

9. The method of claim 1, which comprises measuring at least a 20% increase in the cTnI level during or after exercise as compared the cTnI level at rest.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

His His His His His His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Asp Asp Asp Asp Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Ala Asp Asp Asp Asp Lys
1               5
```